(12) United States Patent
Lee

(10) Patent No.: US 10,799,701 B2
(45) Date of Patent: Oct. 13, 2020

(54) SYSTEMS AND METHODS FOR IDENTIFYING AND TREATING PATIENTS WITH HIGH-FREQUENCY ELECTRICAL SIGNALS

(71) Applicant: Nevro Corp., Redwood City, CA (US)

(72) Inventor: Dongchul Lee, Agua Dulce, CA (US)

(73) Assignee: Nevro Corp., Redwood City, CA (US)

(*) Notice: Subject to any disclaimer, the term of this patent is extended or adjusted under 35 U.S.C. 154(b) by 711 days.

(21) Appl. No.: 15/470,027

(22) Filed: Mar. 27, 2017

(65) Prior Publication Data

US 2017/0291031 A1 Oct. 12, 2017

Related U.S. Application Data

(60) Provisional application No. 62/315,569, filed on Mar. 30, 2016.

(51) Int. Cl.
*A61B 5/00* (2006.01)
*A61N 1/36* (2006.01)
(Continued)

(52) U.S. Cl.
CPC ....... *A61N 1/36142* (2013.01); *A61N 1/0551* (2013.01); *A61N 1/36062* (2017.08); *A61N 1/36071* (2013.01); *A61N 1/36139* (2013.01); *A61N 1/36171* (2013.01); *A61N 1/08* (2013.01); *A61N 1/3605* (2013.01);
(Continued)

(58) Field of Classification Search
CPC ............ A61N 1/36062; A61N 1/36071; A61N 1/36139; A61N 1/36142; A61N 1/0551; A61N 1/0553
See application file for complete search history.

(56) References Cited

U.S. PATENT DOCUMENTS 1,597,061 A 8/1926 Cultra
2,622,601 A 12/1952 Nemec
(Continued)

FOREIGN PATENT DOCUMENTS

GB 2449546 A 11/2008
JP 2007528774 A 10/2007
(Continued)

OTHER PUBLICATIONS

European Extended Search Report and Written Opinion for European Patent No. 17163934.7, Applicant: Nevro Corp., dated Feb. 16, 2018, 7 pages.
(Continued)

*Primary Examiner* — Max F Hindenburg
(74) *Attorney, Agent, or Firm* — Perkins Coie LLP

(57) ABSTRACT

Systems and methods for identifying and treating patients with high frequency electrical signals. A representative method for identifying a patient as a candidate for pain treatment includes identifying a first sensory threshold, delivering an electrical signal to a neural population of the patient at a frequency in a frequency range of 1.5 kHz to 100 kHz and, while and/or after delivering the electrical signal to the patient, identifying a second sensory threshold of the patient. If the second sensory threshold is less than the first, the method can include identifying the patient as a candidate for receiving an electrical signal at a frequency in the foregoing range for pain treatment.

30 Claims, 20 Drawing Sheets

(51) Int. Cl.
 *A61N 1/05* (2006.01)
 *A61N 1/372* (2006.01)
 *A61N 1/08* (2006.01)

(52) U.S. Cl.
 CPC ...... *A61N 1/36034* (2017.08); *A61N 1/36164* (2013.01); *A61N 1/37241* (2013.01)

(56) References Cited

U.S. PATENT DOCUMENTS

| | | |
|---|---|---|
| 3,195,540 A | 7/1965 | Waller |
| 3,817,254 A | 6/1974 | Maurer |
| 3,822,708 A | 7/1974 | Zilber |
| 3,893,463 A | 7/1975 | Williams |
| 4,014,347 A | 3/1977 | Halleck et al. |
| 4,023,574 A | 5/1977 | Nemec |
| 4,055,190 A | 10/1977 | Tany et al. |
| 4,414,986 A | 11/1983 | Dickhudt et al. |
| 4,535,777 A | 8/1985 | Castel |
| 4,541,432 A | 9/1985 | Molina-Negro et al. |
| 4,608,985 A | 9/1986 | Crish et al. |
| 4,649,935 A | 3/1987 | Charmillot et al. |
| 4,841,973 A | 6/1989 | Stecker |
| RE33,420 E | 11/1990 | Sussman et al. |
| 5,002,053 A | 3/1991 | Garcia-Rill |
| 5,335,657 A | 8/1994 | Terry, Jr. et al. |
| 5,354,320 A | 10/1994 | Schaldach et al. |
| 5,514,175 A | 5/1996 | Kim et al. |
| 5,562,717 A | 10/1996 | Tippey et al. |
| 5,643,330 A | 7/1997 | Holsheimer et al. |
| 5,776,170 A | 7/1998 | MacDonald et al. |
| 5,806,522 A | 9/1998 | Katims |
| 5,830,151 A | 11/1998 | Hadzic et al. |
| 5,853,373 A | 12/1998 | Griffith et al. |
| 5,893,883 A | 4/1999 | Torgerson |
| 5,983,141 A | 11/1999 | Sluijter et al. |
| 5,995,872 A | 11/1999 | Bourgeois |
| 6,002,964 A | 12/1999 | Feler et al. |
| 6,014,588 A | 1/2000 | Fitz |
| 6,027,456 A | 2/2000 | Feler et al. |
| 6,161,044 A | 12/2000 | Silverstone |
| 6,167,311 A | 12/2000 | Rezai |
| 6,176,242 B1 | 1/2001 | Rise |
| 6,233,488 B1 | 5/2001 | Hess |
| 6,238,423 B1 | 5/2001 | Bardy |
| 6,246,912 B1 | 6/2001 | Sluijter et al. |
| 6,341,236 B1 | 1/2002 | Osorio et al. |
| 6,356,786 B1 | 3/2002 | Rezai et al. |
| 6,405,079 B1 | 6/2002 | Ansarinia |
| 6,421,566 B1 | 7/2002 | Holsheimer |
| 6,440,090 B1 | 8/2002 | Schallhorn |
| 6,505,078 B1 | 1/2003 | King et al. |
| 6,510,347 B2 | 1/2003 | Borkan |
| 6,571,127 B1 | 5/2003 | Ben-Haim et al. |
| 6,584,358 B2 | 6/2003 | Carter et al. |
| 6,609,030 B1 | 8/2003 | Rezai et al. |
| 6,622,048 B1 | 9/2003 | Mann |
| 6,721,603 B2 | 4/2004 | Zabara et al. |
| 6,795,737 B2 | 9/2004 | Gielen et al. |
| 6,871,090 B1 | 3/2005 | He et al. |
| 6,885,888 B2 | 4/2005 | Rezai |
| 6,907,295 B2 | 6/2005 | Gross et al. |
| 6,923,784 B2 | 8/2005 | Stein |
| 6,928,320 B2 | 8/2005 | King |
| 6,950,707 B2 | 9/2005 | Whitehurst |
| 6,968,237 B2 | 11/2005 | Doan et al. |
| 6,990,376 B2 | 1/2006 | Tanagho et al. |
| 7,024,246 B2 | 4/2006 | Acosta et al. |
| 7,047,079 B2 | 5/2006 | Erickson |
| 7,082,333 B1 | 7/2006 | Bauhahn et al. |
| 7,117,034 B2 | 10/2006 | Kronberg |
| 7,146,224 B2 | 12/2006 | King |
| 7,149,574 B2 | 12/2006 | Yun et al. |
| 7,167,750 B2 | 1/2007 | Knudson et al. |
| 7,174,215 B2 | 2/2007 | Bradley |
| 7,180,760 B2 | 2/2007 | Varrichio et al. |
| 7,206,632 B2 | 4/2007 | King |
| 7,212,865 B2 | 5/2007 | Cory |
| 7,236,822 B2 | 6/2007 | Dobak, III |
| 7,239,912 B2 | 7/2007 | Dobak, III |
| 7,252,090 B2 | 8/2007 | Goetz |
| 7,260,436 B2 | 8/2007 | Kilgore et al. |
| 7,266,412 B2 | 9/2007 | Stypulkowski |
| 7,288,062 B2 | 10/2007 | Spiegel |
| 7,313,440 B2 | 12/2007 | Miesel |
| 7,324,852 B2 | 1/2008 | Barolat et al. |
| 7,326,181 B2 | 2/2008 | Katims |
| 7,333,857 B2 | 2/2008 | Campbell |
| 7,337,005 B2 | 2/2008 | Kim et al. |
| 7,346,398 B2 | 3/2008 | Gross et al. |
| 7,349,743 B2 | 3/2008 | Tadlock |
| 7,363,076 B2 | 4/2008 | Yun et al. |
| 7,389,145 B2 | 6/2008 | Kilgore et al. |
| 7,393,351 B2 | 7/2008 | Woloszko et al. |
| 7,493,172 B2 | 2/2009 | Whitehurst et al. |
| 7,502,652 B2 | 3/2009 | Gaunt et al. |
| 7,580,753 B2 | 8/2009 | Kim et al. |
| 7,599,737 B2 | 10/2009 | Yomtov et al. |
| 7,676,269 B2 | 3/2010 | Yun et al. |
| 7,689,289 B2 | 3/2010 | King |
| 7,734,340 B2 | 6/2010 | De Ridder |
| 7,742,810 B2 | 6/2010 | Moffitt et al. |
| 7,761,170 B2 | 7/2010 | Kaplan et al. |
| 7,778,704 B2 | 8/2010 | Rezai |
| 7,813,803 B2 | 10/2010 | Heruth et al. |
| 7,826,901 B2 | 11/2010 | Lee et al. |
| 7,860,570 B2 | 12/2010 | Whitehurst et al. |
| 7,877,136 B1 | 1/2011 | Moffitt et al. |
| 7,890,176 B2 | 2/2011 | Jaax et al. |
| 7,933,654 B2 | 4/2011 | Merfeld et al. |
| 7,937,145 B2 | 5/2011 | Dobak |
| 8,010,198 B2 | 8/2011 | Libbus et al. |
| 8,027,718 B2 | 9/2011 | Spinner et al. |
| 8,046,075 B2 | 10/2011 | Rezai |
| 8,060,208 B2 | 11/2011 | Kilgore et al. |
| 8,082,038 B2 | 12/2011 | Simon et al. |
| 8,082,039 B2 | 12/2011 | Kim et al. |
| 8,170,675 B2 | 5/2012 | Alataris et al. |
| 8,209,021 B2 | 6/2012 | Alataris et al. |
| 8,209,028 B2 | 6/2012 | Skelton et al. |
| 8,224,453 B2 | 7/2012 | De Ridder |
| 8,255,057 B2 | 8/2012 | Fang et al. |
| 8,280,515 B2 | 10/2012 | Greenspan |
| 8,355,792 B2 | 1/2013 | Alataris et al. |
| 8,359,102 B2 | 1/2013 | Alataris et al. |
| 8,359,103 B2 | 1/2013 | Alataris et al. |
| 8,380,318 B2 | 2/2013 | Kishawi et al. |
| 8,396,559 B2 | 3/2013 | Alataris et al. |
| 8,423,147 B2 | 4/2013 | Alataris et al. |
| 8,428,748 B2 | 4/2013 | Alataris et al. |
| 8,509,905 B2 | 8/2013 | Alataris et al. |
| 8,554,326 B2 | 10/2013 | Alataris et al. |
| 8,694,109 B2 | 4/2014 | Alataris et al. |
| 8,718,781 B2 | 5/2014 | Alataris et al. |
| 8,718,782 B2 | 5/2014 | Alataris et al. |
| 8,768,472 B2 | 7/2014 | Fang et al. |
| 8,774,926 B2 | 7/2014 | Alataris et al. |
| 8,874,217 B2 | 10/2014 | Alataris et al. |
| 8,874,221 B2 | 10/2014 | Alataris et al. |
| 9,220,889 B2 | 12/2015 | Carlton et al. |
| 9,278,215 B2 | 3/2016 | Thacker et al. |
| 9,283,387 B2 | 3/2016 | Thacker et al. |
| 9,283,388 B2 | 3/2016 | Thacker et al. |
| 2002/0055779 A1 | 5/2002 | Andrews |
| 2002/0128700 A1 | 9/2002 | Cross |
| 2003/0120323 A1 | 6/2003 | Meadows et al. |
| 2004/0015202 A1 | 1/2004 | Chandler et al. |
| 2004/0034394 A1 | 2/2004 | Woods et al. |
| 2004/0039425 A1 | 2/2004 | Greenwood-Van Meerveld |
| 2004/0073273 A1 | 4/2004 | Gluckman et al. |
| 2004/0162590 A1 | 8/2004 | Whitehurst et al. |
| 2004/0167584 A1 | 8/2004 | Carroll et al. |
| 2004/0210270 A1 | 10/2004 | Erickson |
| 2005/0033381 A1 | 2/2005 | Carter et al. |
| 2005/0038489 A1 | 2/2005 | Grill |

(56) References Cited

U.S. PATENT DOCUMENTS

| | | |
|---|---|---|
| 2005/0060001 A1 | 3/2005 | Singhal et al. |
| 2005/0113882 A1 | 5/2005 | Cameron et al. |
| 2005/0119713 A1 | 6/2005 | Whitehurst et al. |
| 2005/0143789 A1 | 6/2005 | Whitehurst et al. |
| 2005/0153885 A1 | 7/2005 | Yun et al. |
| 2005/0246006 A1 | 11/2005 | Daniels |
| 2006/0004422 A1 | 1/2006 | De Ridder |
| 2006/0041285 A1 | 2/2006 | Johnson |
| 2006/0074456 A1 | 4/2006 | Pyles et al. |
| 2006/0095088 A1 | 5/2006 | De Ridder |
| 2006/0100671 A1 | 5/2006 | Ridder |
| 2006/0161219 A1 | 7/2006 | Mock et al. |
| 2006/0161235 A1 | 7/2006 | King |
| 2006/0190048 A1 | 8/2006 | Gerber |
| 2006/0229687 A1 | 10/2006 | Goetz et al. |
| 2006/0253182 A1 | 11/2006 | King |
| 2007/0021803 A1 | 1/2007 | Deem et al. |
| 2007/0032827 A1 | 2/2007 | Katims |
| 2007/0039625 A1 | 2/2007 | Heruth et al. |
| 2007/0049991 A1 | 3/2007 | Klostermann et al. |
| 2007/0060954 A1 | 3/2007 | Cameron et al. |
| 2007/0066997 A1 | 3/2007 | He et al. |
| 2007/0073353 A1 | 3/2007 | Rooney et al. |
| 2007/0073354 A1 | 3/2007 | Knudson et al. |
| 2007/0106337 A1 | 5/2007 | Errico et al. |
| 2007/0150034 A1 | 6/2007 | Rooney et al. |
| 2007/0156183 A1 | 7/2007 | Rhodes |
| 2007/0179559 A1 | 8/2007 | Giftakis et al. |
| 2007/0179579 A1 | 8/2007 | Feler et al. |
| 2007/0239226 A1 | 10/2007 | Overstreet |
| 2007/0244522 A1 | 10/2007 | Overstreet |
| 2007/0299482 A1 | 12/2007 | Littlewood et al. |
| 2008/0033511 A1 | 2/2008 | Dobak |
| 2008/0103570 A1 | 5/2008 | Gerber |
| 2008/0167697 A1 | 7/2008 | Johnson |
| 2008/0183259 A1 | 7/2008 | Bly et al. |
| 2008/0234791 A1 | 9/2008 | Arle et al. |
| 2009/0036945 A1 | 2/2009 | Chancellor et al. |
| 2009/0054962 A1 | 2/2009 | Lefler et al. |
| 2009/0132010 A1 | 5/2009 | Kronberg |
| 2009/0157141 A1 | 6/2009 | Chiao et al. |
| 2009/0157149 A1 | 6/2009 | Wahlgren et al. |
| 2009/0198306 A1 | 8/2009 | Goetz et al. |
| 2009/0204173 A1 | 8/2009 | Fang et al. |
| 2009/0281595 A1 | 11/2009 | King et al. |
| 2009/0287274 A1 | 11/2009 | De Ridder |
| 2009/0326611 A1 | 12/2009 | Gillbe |
| 2010/0016929 A1 | 1/2010 | Prochazka |
| 2010/0036454 A1 | 2/2010 | Bennett et al. |
| 2010/0094375 A1 | 4/2010 | Donders et al. |
| 2010/0125313 A1 | 5/2010 | Lee et al. |
| 2010/0137938 A1 | 6/2010 | Kishawi et al. |
| 2010/0191307 A1 | 7/2010 | Fang et al. |
| 2010/0241190 A1 | 9/2010 | Kilgore et al. |
| 2010/0274312 A1 | 10/2010 | Alataris et al. |
| 2010/0274314 A1 | 10/2010 | Alataris et al. |
| 2010/0274315 A1 | 10/2010 | Alataris et al. |
| 2010/0274316 A1 | 10/2010 | Alataris et al. |
| 2010/0274317 A1 | 10/2010 | Parker et al. |
| 2010/0274318 A1 | 10/2010 | Walker et al. |
| 2010/0274320 A1 | 10/2010 | Torgerson |
| 2010/0274326 A1 | 10/2010 | Chitre et al. |
| 2010/0324630 A1 | 12/2010 | Lee et al. |
| 2010/0331916 A1 | 12/2010 | Parramon et al. |
| 2011/0009919 A1 | 1/2011 | Carbunaru et al. |
| 2011/0009923 A1 | 1/2011 | Lee |
| 2011/0022114 A1 | 1/2011 | Navarro |
| 2011/0184486 A1 | 7/2011 | De Ridder |
| 2011/0184488 A1 | 7/2011 | De Ridder |
| 2011/0201977 A1 | 8/2011 | Tass |
| 2011/0276107 A1 | 11/2011 | Simon et al. |
| 2011/0282412 A1 | 11/2011 | Glukhovsky et al. |
| 2012/0089200 A1 | 4/2012 | Ranu et al. |
| 2012/0172946 A1 | 7/2012 | Alataris et al. |
| 2012/0277833 A1 | 11/2012 | Gerber et al. |
| 2012/0283797 A1 | 11/2012 | De Ridder |
| 2013/0006325 A1 | 1/2013 | Woods et al. |
| 2013/0023951 A1 | 1/2013 | Greenspan |
| 2013/0041425 A1 | 2/2013 | Fang et al. |
| 2013/0066411 A1 | 3/2013 | Thacker et al. |
| 2013/0172955 A1 | 7/2013 | Alataris et al. |
| 2013/0204173 A1 | 8/2013 | Kelly et al. |
| 2013/0204323 A1 | 8/2013 | Thacker et al. |
| 2013/0211487 A1 | 8/2013 | Fang et al. |
| 2014/0031896 A1 | 1/2014 | Alataris et al. |
| 2014/0276549 A1* | 9/2014 | Osorio ............... A61M 5/1723 604/503 |
| 2016/0082252 A1 | 3/2016 | Hershey et al. |
| 2016/0175594 A1 | 6/2016 | Min et al. |
| 2017/0036023 A1 | 2/2017 | Parker |

FOREIGN PATENT DOCUMENTS

| | | |
|---|---|---|
| WO | WO-02065896 A2 | 8/2002 |
| WO | WO-02092165 A1 | 11/2002 |
| WO | WO-2007082382 A1 | 7/2007 |
| WO | WO-2007117232 A1 | 10/2007 |
| WO | WO-2008039982 A2 | 4/2008 |
| WO | WO-2008045434 A2 | 4/2008 |
| WO | WO-2008121891 A1 | 10/2008 |
| WO | WO-2011014570 A1 | 2/2011 |
| WO | WO-2013116368 A1 | 8/2013 |

OTHER PUBLICATIONS

Kilgore et al. "Nerve Conduction Block Utilizing High-Frequency Alternating Current" Medical & Biology Engineering and Computing, 2004, vol. 42, pp. 394-406.

Alo et al., "New Trends in Neuromodulation for the Management of Neuropathic Pain," Neurosurgery, vol. 50, No. 4, Apr. 2002, 15 pages.

Bahdra et al., Stimulation of High-Frequency Sinusoidal Electrical Block of Mammalian Myelinated Axons, J Comput Neurosco, 22:313-326, 2007.

Barolat et al., "Multifactorial Analysis of Epidural Spinal Cord Stimulation,"Sterotactic and Functional Neurosurgery, 1991; 56: 77-103.

Bhadra et al., "High Frequency electrical conduction block of the pudendal nerve," Journal of Neural Engineering—Institute of Physics Publishing, 2006, 8 pages.

Bhadra MD, Niloy et al., "High-Frequency Electrical Conduction Block of Mammalian Peripheral Motor Nerve," Muscle and Nerve, Dec. 2005, 9 pages.

Boger et al., "Bladder Voiding by Combined High Frequency Electrical Pudendal Nerve Block and Sacral Root Stimulation," Neurourology and Urodynamics, 27, 2008, 5 pages.

Bowman and McNeal, Response of Single Alpha Motoneurons to High-Frequency Pulse Trains, Appl. Neurophysiol. 49, p. 121-138, 1986, 10 pages.

Burton, Charles, "Dorsal Column Stimulation: Optimization of Application," Surgical Neurology, vol. 4, No. 1, Jul. 1975, 10 pages.

Cuellar et al., "Effect of High Frequency Alternating Current on Spinal Afferent Nociceptive Transmission," Neuromodulation: Technology at the Neural Interface, 2012, 10 pages.

DeRidder et al., "Are Paresthesias necessary for pain suppression in SCS—Burst Stimulation," BRAIN, Brain Research Center Antwerp of Innovative and Interdisciplinary Neuromodulation, 2010, 27 pages.

DeRidder et al., "Burst Spinal Cord Stimulation: Toward Paresthesia-Free Pain Suppression," www.neurosurgery-online.com, vol. 66, Nos. 5, May 2010, 5 pages.

Grill, Warren et al., "Stimulus Waveforms for Selective Neural Stimulation," IEEE Engineering in Medicine and Biology, Jul./Aug. 1995, pp. 375-385.

Holsheimer—Effectiveness of Spinal Cord Stimulation in the Management of Chronic Pain: Analysis of Technical Drawbacks and Solutions, Neurosurgery, vol. 40, No. 5, May 1997, pp. 990-999.

(56) References Cited

OTHER PUBLICATIONS

Hopp et al., "Effect of anodal blockade of myelinated fibers on vagal c-fiber afferents," American Journal Physiological Society, Nov. 1980; 239(5), 9 pages.
Hoppenstein, Reuben, "Electrical Stimulation of the Ventral and Dorsal Columns of the Spinal Cord for Relief of Chronic Intractable Pain: Preliminary Report," Surgical Neurology, vol. 4, No. 1, Jul. 1975, 9 pages.
Huxely et al., "Excitation and Conduction in Nerve: Quantitative Analysis," Science, Sep. 11, 1964; 145: 1154-9.
Jang et al., "Analysis of Failed Spinal Cord Stimulation Trails in the Treatment of Intractable Chronic Pain," J. Korean Neurosurg Soc 43, 2008, 5 pages.
Kilgore et al. "Nerve Conduction Block Utilizing High-Frequency Alternating Current" Medical & Biology Engineering and Computing, 2004, vol. 24, pp. 394-406.
Kilgore et al. "Reversible Nerve Conduction Block Using Kilohertz Frequency Alternating Current," Neuromodulation Technology at the Neural Interface, International Neuromodulation Society, 2013, 13 pages.
Kumar et al., "Spinal Cord Stimulation in Treatment of Chronic Benign Pain: Challenges in Treatment Planning and Present Status, a 22-Year Experience," Neurosurgery, vol. 58, No. 3, Mar. 2006, 16 pages.
Lachance et al., "Stimulation-induced ectopicity and propagation windows in model damaged axons," J. Comput Neurosci, 2014, 9 pages.
Linderoth et al., "Mechanisms of Spinal Cord Stimulation in Painful Syndromes: Role of Animal Models," Pain Medicine, vol. 7, No. S1, 2006, 13 pages.
Linderoth et al., "Physiology of Spinal Cord Stimulation: Review and Update," Neuromodulation, vol. 2, No. 3, 1999, 15 pages.
Mediati, R.D., , "Mechanisms of Spinal Cord Stimulation," Florence, Oct. 2, 2002, 31 pages.
Melzack, Ronald et al., "Pain Mechanisms: A New Theory," Science, vol. 150, No. 3699, Nov. 19, 1965, 9 pages.
Muller and Hunsperger, "Helvetica Physiologica Acta—Reversible Blockierung der Erregungsleitung im Nerven durch Mittelfrequenz—Daverstrom," Schwabe & Co. Basel, vol. 25, Fasc. 1, 1967, 4 pages.
North et al., "Failed Back Surgery Syndrome: 5-year Follow-Up after Spinal Cord Stimulator Implantation," Neurosurgery, Official Journal of the Congress of Neurological Surgeons, vol. 28, No. 5, May 1991, 9 pages.
North et al., "Spinal Cord Stimulation for Axial Low Back Pain," SPINE, vol. 30, No. 12, 2005, 7 pages.
North et al., "Spinal Cord Stimulation for Chronic, Intractable Pain: Experience over Two Decades," Neurosurgery, vol. 32, No. 2, Mar. 1993, 12 pages.
Oakley, John C., "Spinal Cord Stimulation Mechanisms of Action," SPINE vol. 27, No. 22, copyright 2002, 10 pages.
Perruchoud et al., "Analgesic Efficacy of High-Frequency Spinal Cord Stimulation: A Randomized Double-Blind Placebo-Controlled Study," Neuromodulation: Technology at Neural Interface, International Neuromodulation Society, 2013, 7 pages.
Shealy MD, C. Norman et al., "Electrical Inhibition of Pain by Stimulation of the Dorsal Columns: Preliminary Clinical Report," Anesthesia and Analgesia . . . Current Researches, vol. 446, No. 4, Jul.-Aug. 1967, 3 pages.
Simpson, BA, "Spinal Cord Stimulation in 60 cases of Intractable Pain." Journal of Neurology, Neurosurgery and Psychiatry, 1991; 54 pp. 196-199.
Simpson, BA, "Spinal Cord Stimulation." British Journal of Neurosurgery, Feb. 11, 1997 (1), 5-11, 7 pages.
Solomonow et al., "Control of Muscle Contractile Force through Indirect High-Frequency Stimulation," AM Journal of Physical Medicine, 1983, vol. 62, No. 3, pp. 71-82.
Tanner, J.A., "Reversible blocking of nerve conduction by alternating-current excitation," Nature, Aug. 18, 1962; 195: 712-3.
Tiede et al., "Novel Spinal Cord Stimulation Parameters in Patients with Predominate Back Pain," Neuromodulation: Technology at the Neural Interface, 2013, 6 pages.
Urban et al., "Percutaneous epidural stimulation of the spinal cord for relief of pain—Long Term Results," Journal of Neurosurgery, vol. 48, Mar. 1978, 7 pages.
Van Butyen et al., "High Frequency Spinal Cord Stimulation for the Treatment of Chronic Back Pain Patients: Results of a Prospective Multicenter European Clinical Study," Neuromodulation Technology at the Neural Interface, International Neuromodulation Society, 2012, 8 pages.
Van Den Honert, Mortimer JT, "A Technique for Collision Block of Peripheral Nerve: Frequency Dependence," MP-11 IEEE Trans. Biomed, Eng. 28: 379-382, 1981.
Wallin et al., "Spinal Cord Stimulation inhibits long-term potentiation of spinal wide dynamic range neurons," Elsevier Science B.V., Brain Research, 5 pages 2003.
Wolter et al., "Continuous Versus Intermittent Spinal Cord Stimulation: An Analysis of Factors Influencing Clinical Efficacy," Neuromodulation: Technology at Neural Interface, www.neuromodulationjournal.com, 2011, 8 pages.
Woo MY, Campbell B. "Asynchronous Firing and Block of Peripheral Nerve Conduction by 20KC Alternating Current," Los Angeles Neuro Society, Jun. 1964; 87-94, 5 pages.
Zhang et al., "Simulation Analysis of Conduction Block in Myelinated Axons Induced by High-Frequency Biphasic Rectangular Pulses," IEEE Transactions on Biomedical Engineering, vol. 53., No. 7, Jul. 2006, 4 pages.
Zhu et al., "Changes in functional properties of A-type but not C-type sensory neurons in vivo in a rat model of peripheral neuropathy," Journal of Pain Research, Dovepress, 2012, 18 pages.
Zhu et al., "Early Demyelination of Primary A-Fibers Induces a Rapid-Onset of Neuropathic Pain in Rat," Neuroscience 200, 2012, 13 pages.
Zhu et al., "Excitability of Aβ sensory neurons is altered in an animal model of peripheral neuropathy," BMC Neuroscience, 13:15, 2012, 15 pages.
International Search Report and Written Opinion for International Patent Application No. PCT/US2020/014160, Applicant: Nevro Corp., dated Jun. 4, 2020, 13 pages.
U.S. Appl. No. 16/746,556, filed Jan. 17, 2020, Lee.

* cited by examiner

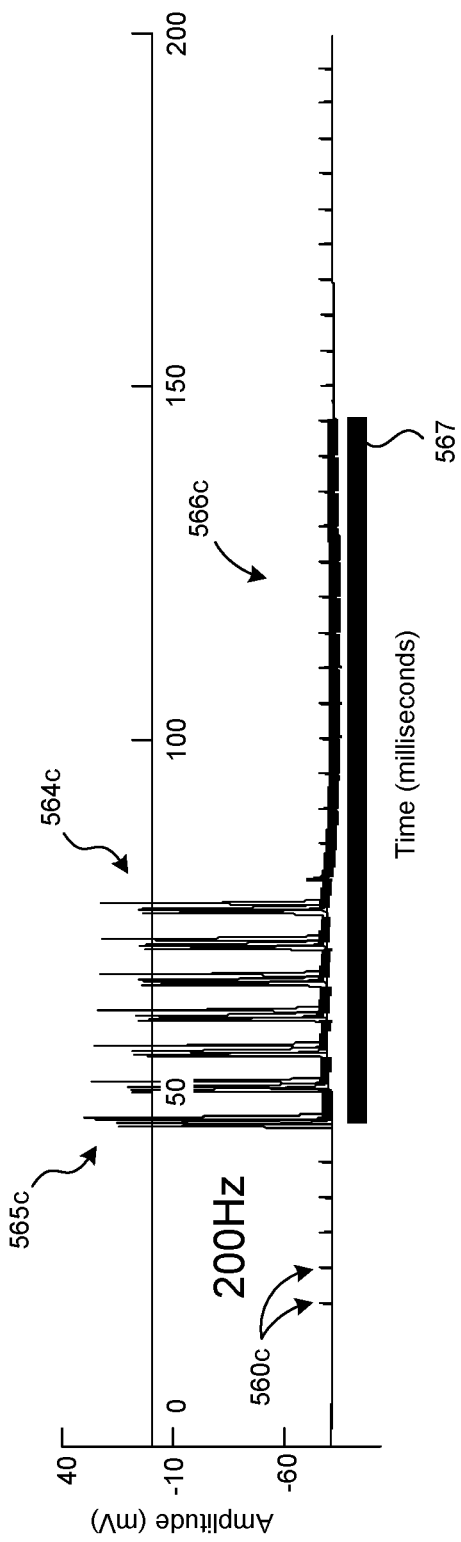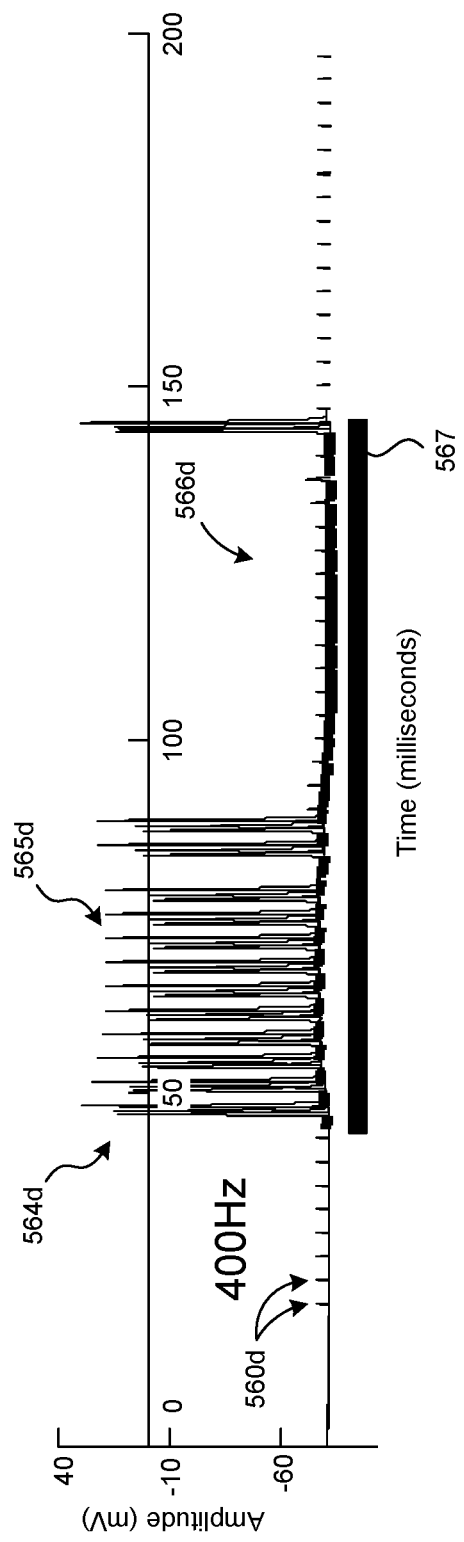
FIG. 5C
FIG. 5D

SYSTEMS AND METHODS FOR IDENTIFYING AND TREATING PATIENTS WITH HIGH-FREQUENCY ELECTRICAL SIGNALS

CROSS-REFERENCE TO RELATED APPLICATION

The present application claims priority to U.S. Provisional Patent Application No. 62/315,569, filed on Mar. 30, 2016, and incorporated herein by reference.

TECHNICAL FIELD

The present technology is directed generally to systems and methods for identifying and treating patients with high-frequency electrical signals. Particular embodiments include detecting a change in a patient's sensory threshold level resulting from administering a high-frequency signal to the patient, and/or targeting the patient's axons during treatment.

BACKGROUND

Neurological stimulators have been developed to treat pain, movement disorders, functional disorders, spasticity, cancer, cardiac disorders, and various other medical conditions. Implantable neurological stimulation systems generally have an implantable signal generator and one or more leads that deliver electrical pulses to neurological tissue or muscle tissue. For example, several neurological stimulation systems for spinal cord stimulation (SCS) have cylindrical leads that include a lead body with a circular cross-sectional shape and one or more conductive rings (i.e., contacts) spaced apart from each other at the distal end of the lead body. The conductive rings operate as individual electrodes and, in many cases, the SCS leads are implanted percutaneously through a needle inserted into the epidural space, with or without the assistance of a stylet.

Once implanted, the signal generator applies electrical pulses to the electrodes, which in turn modify the function of the patient's nervous system, such as by altering the patient's responsiveness to sensory stimuli and/or altering the patient's motor-circuit output. In SCS therapy for the treatment of pain, the signal generator applies electrical pulses to the spinal cord via the electrodes. In conventional SCS therapy, electrical pulses are used to generate sensations (known as paresthesia) that mask or otherwise alter the patient's sensation of pain. For example, in many cases, patients report paresthesia as a tingling sensation that is perceived as less uncomfortable than the underlying pain sensation.

In contrast to traditional or conventional (i.e., paresthesia-based) SCS, a form of paresthesia-free SCS has been developed that uses therapy signal parameters for treating the patient's sensation of pain without generating paresthesia or otherwise using paresthesia to mask the patient's sensation of pain. In addition to avoiding paresthesia, such techniques have been demonstrated to improve patient outcomes and increase the fraction of patients who successfully respond to spinal cord stimulation. Nevertheless, there remains a need to further advance paresthesia-free SCS systems and methods so as to improve upon the results obtained to date.

BRIEF DESCRIPTION OF THE DRAWINGS

FIGS. 5A-5D illustrate response curves based on data received at the recording nodes shown in FIG. 4, with test pulses injected at a variety of frequencies in accordance with several embodiments of the present technology.

DETAILED DESCRIPTION

Aspects of the present technology include simulating a degenerated neuron's response to a high-frequency therapy signal, and, based on the results of the simulations, techniques for screening patients suitable for receiving such signals, and/or adjusting the parameters of such signals, and/or preferentially directing such signals to the axons of the patient's neurons. In particular embodiments, the screening technique and/or adjusting technique can exploit an expected change in the patient's response to sensory stimuli as a result of receiving stimulation at high frequencies (e.g., from about 1.5 kHz to about 100 kHz).

General aspects of the environments in which the disclosed technology operates are described below under Heading 1.0 ("Overview") with reference to FIGS. 1A and 1B. Particular embodiments of the technology are described further under Heading 2.0 ("Representative Embodiments") with reference to FIGS. 2A-10. Additional embodiments are described under Heading 3.0 ("Additional Embodiments").

1.0 Overview

One example of a paresthesia-free SCS therapy system is a "high frequency" SCS system. High frequency SCS systems can inhibit, reduce, and/or eliminate pain via waveforms with high frequency elements or components (e.g., portions having high fundamental frequencies), generally with reduced or eliminated side effects. Such side effects can include unwanted paresthesia, unwanted motor stimulation or blocking, unwanted pain or discomfort, and/or interference with sensory functions other than the targeted pain. In a representative embodiment, a patient may receive high frequency therapeutic signals with at least a portion of the therapy signal at a frequency of from about 1.5 kHz to about 100 kHz, or from about 1.5 kHz to about 50 kHz, or from about 3 kHz to about 20 kHz, or from about 5 kHz to about 15 kHz, or at frequencies of about 8 kHz, 9 kHz, or 10 kHz. These frequencies are significantly higher than the frequencies associated with conventional "low frequency" SCS, which are generally below 1,200 Hz, and more commonly below 100 Hz. Accordingly, modulation at these and other representative frequencies (e.g., from about 1.5 kHz to about 100 kHz) is occasionally referred to herein as "high frequency stimulation," "high frequency SCS," and/or "high frequency modulation." Further examples of paresthesia-free SCS systems are described in U.S. Patent Publication Nos. 2009/0204173 and 2010/0274314, the respective disclosures of which are herein incorporated by reference in their entireties.

Figure 1A:
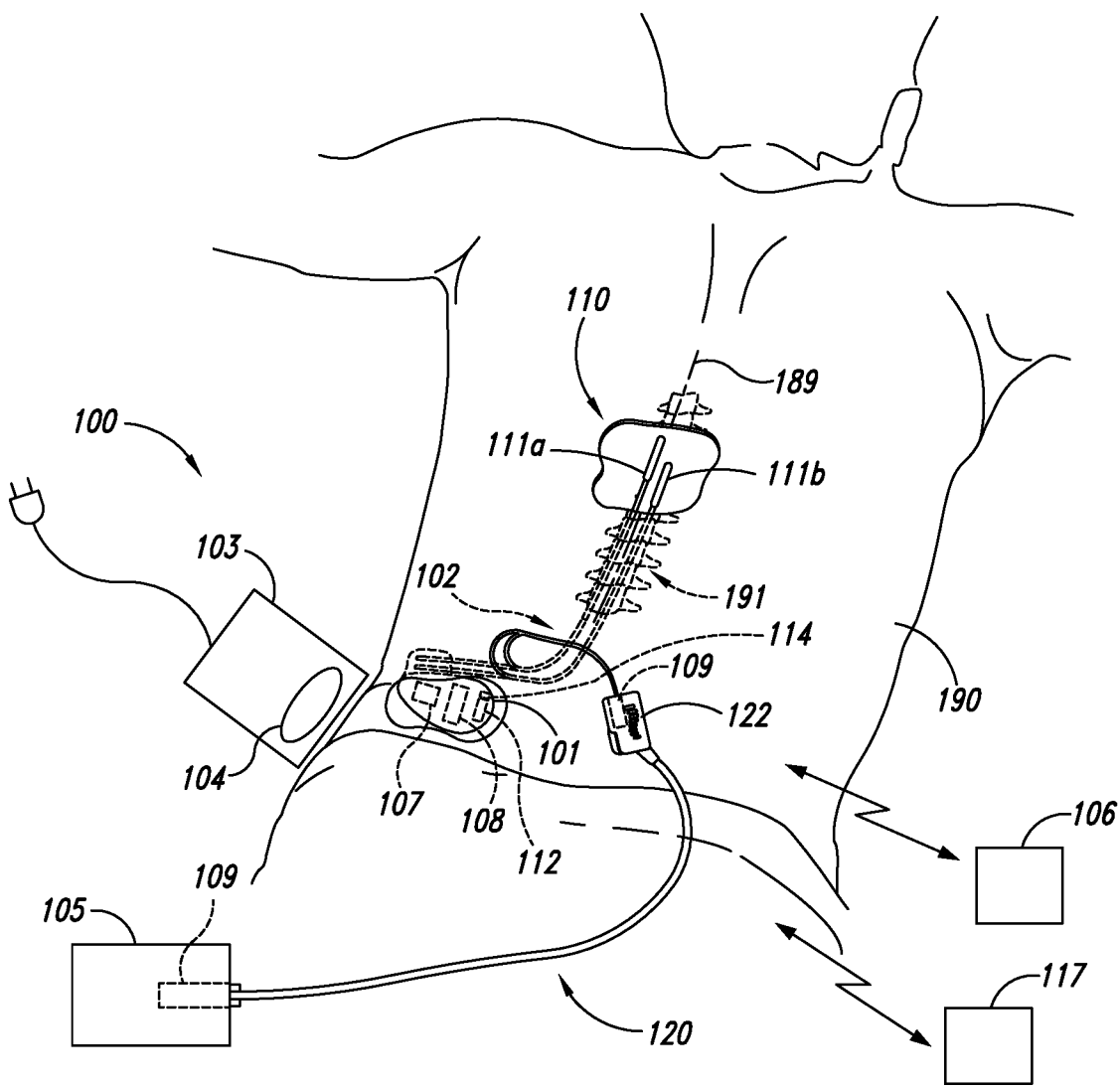
FIG. 1A is a partially schematic illustration of an implantable spinal cord modulation system positioned at a patient's spine to deliver therapeutic signals in accordance with several embodiments of the present technology.

FIG. 1A schematically illustrates a representative patient therapy system 100 for providing relief from chronic pain and/or other conditions, arranged relative to the general anatomy of a patient's spinal column 191. The system 100 can include a signal generator 101 (e.g., an implanted or implantable pulse generator or IPG), which may be implanted subcutaneously within a patient 190 and coupled to one or more signal delivery elements or devices 110. The signal delivery elements or devices 110 may be implanted within the patient 190, typically at or near the patient's spinal cord midline 189. The signal delivery elements 110 carry features for delivering therapy to the patient 190 after implantation. The signal generator 101 can be connected directly to the signal delivery devices 110, or it can be coupled to the signal delivery devices 110 via a signal link or lead extension 102. In a further representative embodiment, the signal delivery devices 110 can include one or more elongated lead(s) or lead body or bodies 111 (identified individually as a first lead 111a and a second lead 111b). As used herein, the terms signal delivery device, lead, and/or lead body include any of a number of suitable substrates and/or support members that carry electrodes/devices for providing therapy signals to the patient 190. For example, the lead or leads 111 can include one or more electrodes or electrical contacts that direct electrical signals into the patient's tissue, e.g., to provide for therapeutic relief. In other embodiments, the signal delivery elements 110 can include structures other than a lead body (e.g., a paddle) that also direct electrical signals and/or other types of signals to the patient 190.

In a representative embodiment, one signal delivery device may be implanted on one side of the spinal cord midline 189, and a second signal delivery device may be implanted on the other side of the spinal cord midline 189. For example, the first and second leads 111a, 111b shown in FIG. 1A may be positioned just off the spinal cord midline 189 (e.g., about 1 mm offset) in opposing lateral directions so that the two leads 111a, 111b are spaced apart from each other by about 2 mm. The first and second leads 111a, 111b may be offset from each other axially (e.g., in a rostral-caudal direction) to provide the practitioner with a greater range of target neural populations. In particular embodiments, the leads 111 may be implanted at a vertebral level ranging from, for example, about T8 to about T12 (e.g., to treat lower back pain and/or leg pain). In other embodiments, one or more signal delivery devices can be implanted at other vertebral levels, e.g., as disclosed in U.S. Patent Application Publication No. 2013/0066411, which is incorporated herein by reference in its entirety.

The signal generator 101 can transmit signals (e.g., electrical signals) to the signal delivery elements 110 that up-regulate (e.g., excite) and/or down-regulate (e.g., block or suppress) target nerves. As used herein, and unless otherwise noted, the terms "modulate," "modulation," "stimulate," and "stimulation" refer generally to signals that have either type of the foregoing effects on the target nerves. The signal generator 101 can include a machine-readable (e.g., computer-readable) or controller-readable medium containing instructions for generating and transmitting suitable therapy signals. The signal generator 101 and/or other elements of the system 100 can include one or more processor(s) 107, memory unit(s) 108, signal generation circuitry 114, and/or input/output device(s) 112. Accordingly, the process of providing modulation signals, providing guidance information for positioning the signal delivery devices 110, establishing battery charging and/or discharging parameters, and/or executing other associated functions can be performed by computer-executable instructions contained by, on or in computer-readable media located at the pulse generator 101 and/or other system components, which may be implanted or external to the patient. Further, the pulse generator 101 and/or other system components may include dedicated hardware, firmware, and/or software for executing computer-executable instructions that, when executed, perform any one or more methods, processes, and/or sub-processes described herein; e.g., the methods, processes, and/or sub-processes described with reference to FIGS. 2A-14 below. The dedicated hardware, firmware, and/or software also serve as "means for" performing the methods, processes, and/or sub-processes described herein. The signal generator 101 can also include multiple portions, elements, and/or subsystems (e.g., for directing signals in accordance with multiple signal delivery parameters), carried in a single housing, as shown in FIG. 1A, or in multiple housings.

The signal generator 101 can also receive and respond to an input signal received from one or more sources. The input signals can direct or influence the manner in which the therapy, charging, and/or process instructions are selected, executed, updated, and/or otherwise performed. The input signals can be received from one or more sensors (e.g., an input device 112 shown schematically in FIG. 1A for purposes of illustration) that are carried by the signal generator 101 and/or distributed outside the signal generator 101 (e.g., at other patient locations) while still communicating with the signal generator 101. The sensors and/or other input devices 112 can provide inputs that depend on or reflect patient state (e.g., patient position, patient posture, and/or patient activity level), and/or inputs that are patient-independent (e.g., time). Still further details are included in U.S. Pat. No. 8,355,797, incorporated herein by reference in its entirety.

In some embodiments, the signal generator 101 and/or signal delivery devices 110 can obtain power to generate the therapy signals from an external power source 103. In one embodiment, for example, the external power source 103 can by-pass an implanted signal generator and generate a therapy signal directly at the signal delivery devices 110 (or via signal relay components). The external power source 103 can transmit power to the implanted signal generator 101 and/or directly to the signal delivery devices 110 using electromagnetic induction (e.g., RF signals). For example, the external power source 103 can include an external coil 104 that communicates with a corresponding internal coil (not shown) within the implantable signal generator 101, signal delivery devices 110, and/or a power relay component (not shown). The external power source 103 can be portable for ease of use.

In another embodiment, the signal generator 101 can obtain the power to generate therapy signals from an internal power source, in addition to or in lieu of the external power source 103. For example, the implanted signal generator 101 can include a non-rechargeable battery or a rechargeable battery to provide such power. When the internal power source includes a rechargeable battery, the external power source 103 can be used to recharge the battery. The external power source 103 can in turn be recharged from a suitable power source (e.g., conventional wall power).

During at least some procedures, an external stimulator or trial modulator 105 can be coupled to the signal delivery elements 110 during an initial procedure, prior to implanting the signal generator 101. For example, a practitioner (e.g., a physician and/or a company representative) can use the trial modulator 105 to vary the modulation parameters provided to the signal delivery elements 110 in real time, and select optimal or particularly efficacious parameters. These parameters can include the location from which the electrical signals are emitted, as well as the characteristics of the electrical signals provided to the signal delivery devices 110. In some embodiments, input is collected via the external stimulator or trial modulator and can be used by the clinician to help determine what parameters to vary. In a typical process, the practitioner uses a cable assembly 120 to temporarily connect the trial modulator 105 to the signal delivery device 110. The practitioner can test the efficacy of the signal delivery devices 110 in an initial position. The practitioner can then disconnect the cable assembly 120 (e.g., at a connector 122), reposition the signal delivery devices 110, and reapply the electrical signals. This process can be performed iteratively until the practitioner obtains the desired position for the signal delivery devices 110. Optionally, the practitioner may move the partially implanted signal delivery devices 110 without disconnecting the cable assembly 120. Furthermore, in some embodiments, the iterative process of repositioning the signal delivery devices 110 and/or varying the therapy parameters may not be performed.

The signal generator 101, the lead extension 102, the trial modulator 105 and/or the connector 122 can each include a receiving element 109. Accordingly, the receiving elements 109 can be patient implantable elements, or the receiving elements 109 can be integral with an external patient treatment element, device or component (e.g., the trial modulator 105 and/or the connector 122). The receiving elements 109 can be configured to facilitate a simple coupling and decoupling procedure between the signal delivery devices 110, the lead extension 102, the signal generator 101, the trial modulator 105 and/or the connector 122. The receiving elements 109 can be at least generally similar in structure and function to those described in U.S. Patent Application Publication No. 2011/0071593, incorporated by reference herein in its entirety.

After the signal delivery elements 110 are implanted, the patient 190 can receive therapy via signals generated by the trial modulator 105, generally for a limited period of time. During this time, the patient wears the cable assembly 120 and the trial modulator 105 outside the body. Assuming the trial therapy is effective or shows the promise of being effective, the practitioner then replaces the trial modulator 105 with the implanted signal generator 101, and programs the signal generator 101 with therapy programs selected based on the experience gained during the trial period. Optionally, the practitioner can also replace the signal delivery elements 110. Once the implantable signal generator 101 has been positioned within the patient 190, the therapy programs provided by the signal generator 101 can still be updated remotely via a wireless physician's programmer (e.g., a physician's laptop, a physician's remote or remote device, etc.) 117 and/or a wireless patient programmer 106 (e.g., a patient's laptop, patient's remote or remote device, etc.). These external devices may also be used to conduct several of the processes described later, e.g., processes for adjusting signal delivery parameters, including via responses to sensory stimuli. Generally, the patient 190 has control over fewer parameters than does the practitioner. For example, the capability of the patient programmer 106 may be limited to starting and/or stopping the signal generator 101, and/or adjusting the signal amplitude. The patient programmer 106 may be configured to accept pain relief input as well as other variables, such as medication use.

In any of the foregoing embodiments, the parameters in accordance with which the signal generator 101 provides signals can be adjusted during portions of the therapy regimen. For example, the frequency, amplitude, pulse width, and/or signal delivery location can be adjusted in accordance with a pre-set therapy program, patient and/or physician inputs, and/or in a random or pseudorandom manner. Such parameter variations can be used to address a number of potential clinical situations. Certain aspects of the foregoing systems and methods may be simplified or eliminated in particular embodiments of the present disclosure. Further aspects of these and other expected beneficial results are detailed in U.S. Patent Application Publication Nos. 2010/0274314; 2009/0204173; and 2013/0066411 (all previously incorporated by reference) and U.S. Patent Application Publication No. 2010/0274317, which is incorporated herein by reference in its entirety.

Figure 1B:
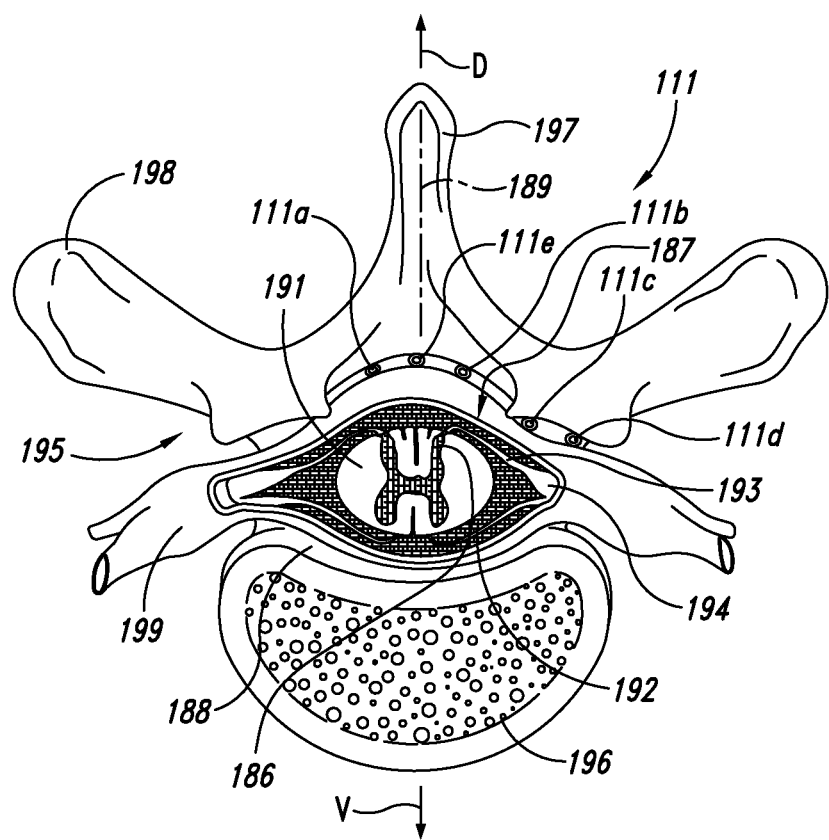
FIG. 1B is a partially schematic, cross-sectional illustration of the patient's spine, illustrating representative locations for implanted lead bodies in accordance with embodiments of the present technology.

FIG. 1B is a cross-sectional illustration of the spinal cord 191 and an adjacent vertebra 195 (based generally on information from Crossman and Neary, "Neuroanatomy," 1995 (published by Churchill Livingstone)), along with multiple leads 111 (shown as leads 111a-111e) implanted at representative locations. For purposes of illustration, multiple leads 111 are shown in FIG. 1B implanted in a single patient. In actual use, any given patient will likely receive fewer than all the leads 111 shown in FIG. 1B.

The spinal cord 191 is situated within a vertebral foramen 188, between a ventrally located ventral body 196 and a dorsally located transverse process 198 and spinous process 197. Arrows V and D identify the ventral and dorsal directions, respectively. The spinal cord 191 itself is located within the dura mater 199, which also surrounds portions of the nerves exiting the spinal cord 191, including the ventral roots 192, dorsal roots 193 and dorsal root ganglia 194. The dorsal roots 193 enter the spinal cord 191 at the dorsal root entry zone 187, and communicate with dorsal horn neurons located at the dorsal horn 186. In one embodiment, the first and second leads 111a, 111b are positioned just off the spinal cord midline 189 (e.g., about 1 mm. offset) in opposing lateral directions so that the two leads 111a, 111b are spaced apart from each other by about 2 mm, as discussed above. In other embodiments, a lead or pairs of leads can be positioned at other locations, e.g., toward the outer edge of the dorsal root entry zone 187 as shown by a third lead 111c, or at the dorsal root ganglia 194, as shown by a fourth lead 111d, or approximately at the spinal cord midline 189, as shown by a fifth lead 111e.

2.0 Representative Embodiments

Systems of the type described above have been used to provide paresthesia-free pain relief to patients suffering from a variety of indications, including low back pain and leg pain. Several possible mechanisms by which high frequency stimulation produces such results have been proposed. Without being bound by theory, the present disclosure describes a potential mechanism in which the therapy signal particularly targets the axons of the patient's neurons.

Figure 2A:
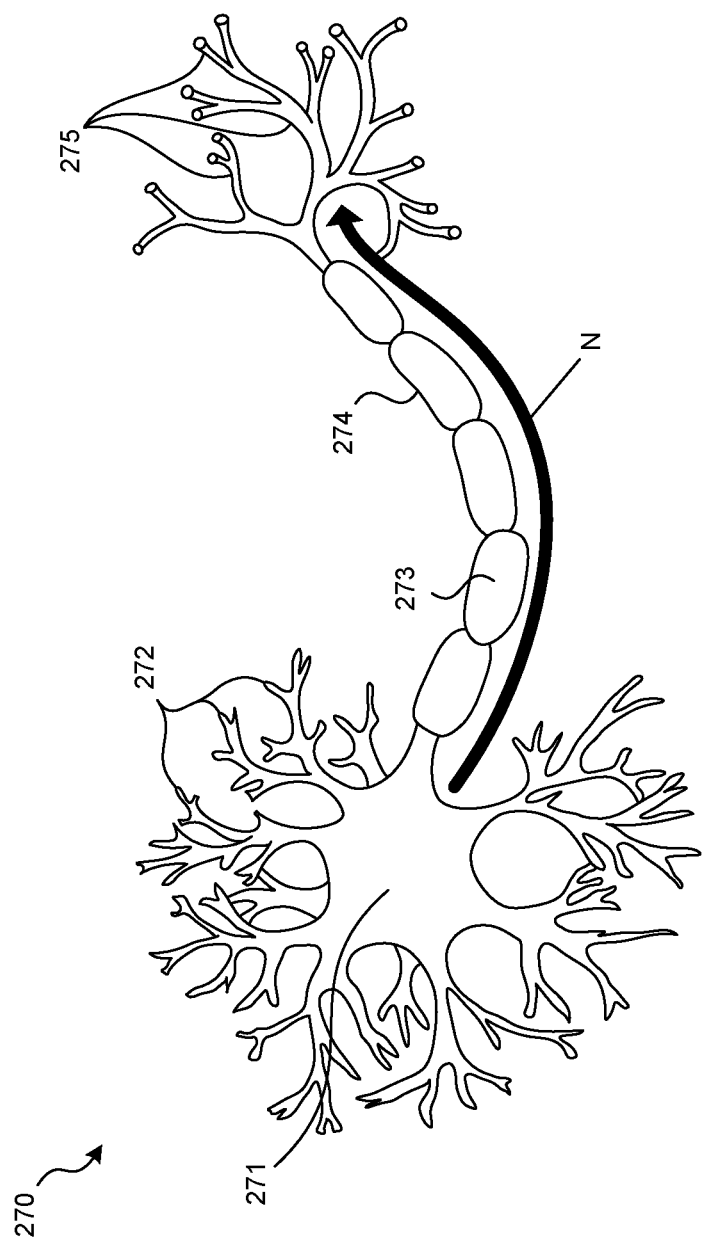
FIG. 2A is a partially schematic illustration of a representative human neuron.

FIG. 2A illustrates a representative human neuron 270. The neuron 270 includes a soma 271, from which dendrites 272 and an axon 273 extend. The dendrites 272 receive incoming neural impulses (messages) from other cells, and the axon transmits the impulses to still further cells via terminal branches 275. A representative neural impulse is illustrated schematically by arrow N in FIG. 2A. The axon 273 can include a myelin sheath 274 that improves the efficiency with which signals are transmitted along the axon 273, e.g., by restricting or preventing noise or other signals from interfering with the neural impulse N.

Neuropathic diseases can cause the neuron 270 to degenerate and therefore reduce the ability of the neuron 270 to successfully transmit impulses along the axon 273. One source (though not the only source) for neural degeneration includes degeneration of the myelin sheath 274. Aspects of the present technology, described further below, include computationally simulating a degenerated neuron, and then simulating the effect of high frequency signals on the ability of the neuron to transmit impulses.

Figure 2B:
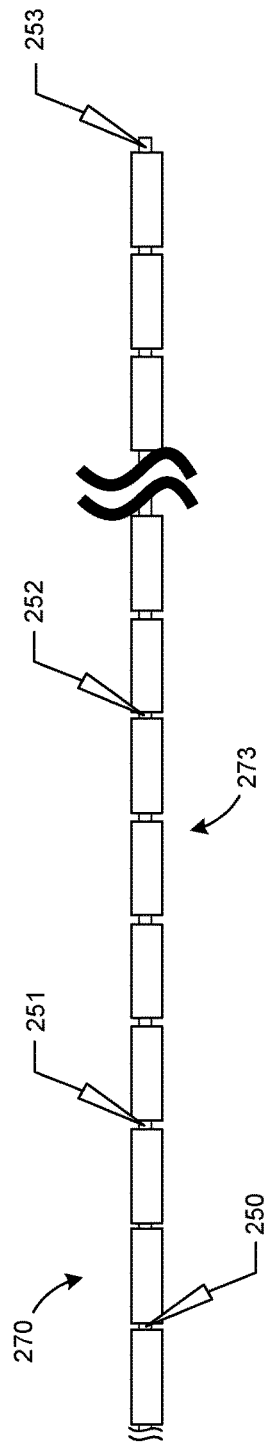
FIG. 2B schematically illustrates a simulated axon of a representative neuron in a computational model for evaluating therapies in accordance with embodiments of the present technology.

FIG. 2B schematically illustrates a portion of a computational model of the neuron 270 shown in FIG. 2A. The model is generally similar to a "McIntyre" model; however, the sodium conductivity constant of the modeled neuron has been reduced from that of a normal neuron, to reflect degeneration of the neuron. A typical value for the sodium conductivity constant in a healthy neuron is approximately 3.0 based on recent publications. In the following simulations, the constant was reduced to 1.8. In a representative simulation, the simulated axon fiber had a diameter of 15 microns. In other embodiments, the diameter of the axon can have other values typically considered as "large," e.g. diameters associated with A fibers (alpha: 12-20 µm, beta: 6-12 µm, and/or gamma: 1-6 µm in diameter), but typically not C fibers.

In addition to simulating the degenerated state of a neuron, the computational model also simulates neural impulses ("test pulses" or "test signals") that a normal neuron would be expected to transmit. In the simulation, a test signal or test pulse was introduced (e.g., "injected") at an injection node 250. As used herein, the term "inject" refers not to a liquid injection but to an electrical signal injection. The ability of the axon 273 to transmit the injected test signal can be measured at multiple recording nodes positioned at selected locations along the axon 273 away from the injection node 250. Representative recording nodes are illustrated as a first recording node 251, a second recording node 252, and a third recording node 253. If the test signal is successfully transmitted, the test signal will appear first at the first recording node 251, then at the second recording node 252, and then at the third recording node 253.

Figure 2C:
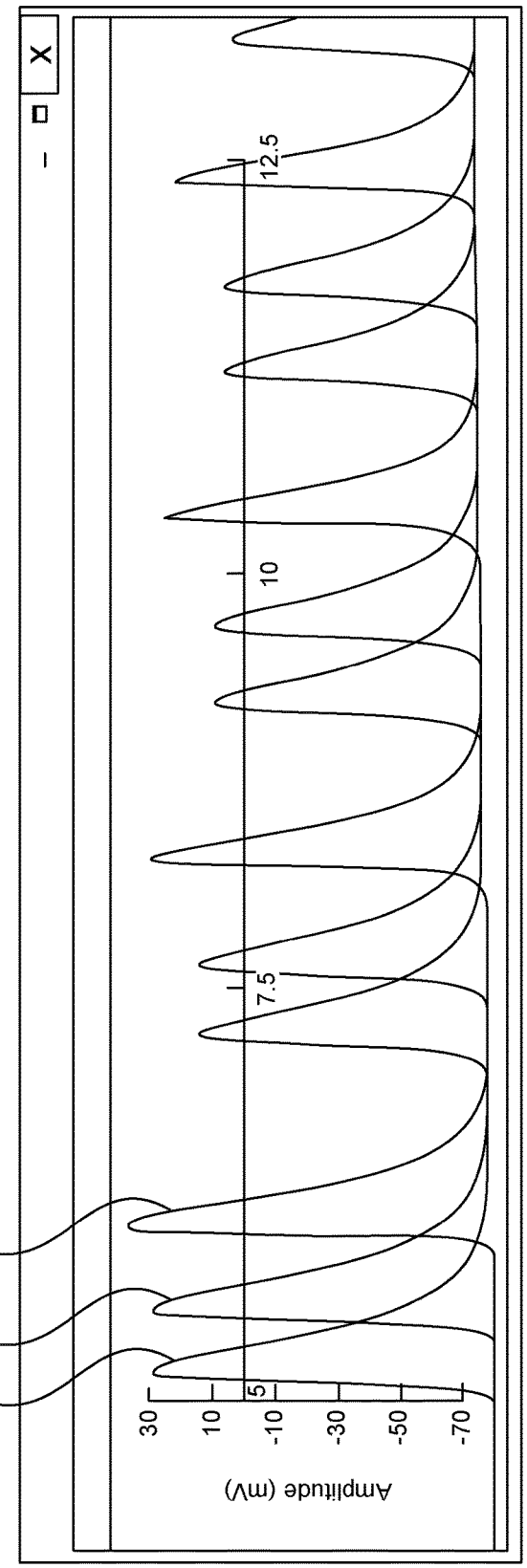
FIG. 2C is a graph illustrating results from running a computational model, including recorded signals along the axon shown in FIG. 2B.

FIG. 2C is a graph illustrating the strengths of the signals received at each of the first-third recording nodes 251-253 as a function of time. The vertical scale illustrates the millivolt level of the signal, with the resting potential of the neuron 270 at approximately −70 millivolts. The horizontal axis identifies the elapsed time (in milliseconds) from an initial signal injection at the injection node 250 (FIG. 2B).

FIG. 2C illustrates a first response curve 261, a second response curve 262, and a third response curve 263. Each response curve corresponds to a signal recorded at the corresponding recording node 251, 252, 253 respectively (FIG. 2B). As shown in FIG. 2C, the effect of a test pulse initially injected at the injection node 250 is first recorded at the first recording node 251, then at the second recording node 252, and then at the third recording node 253, as indicated by successive spikes in the first, second and third response curves 261, 262, 263, respectively. Each successive pulse injected at the injection node 250 produces a corresponding trio of pulses, one at each of the recording nodes 251, 252, 253.

Figure 3A:
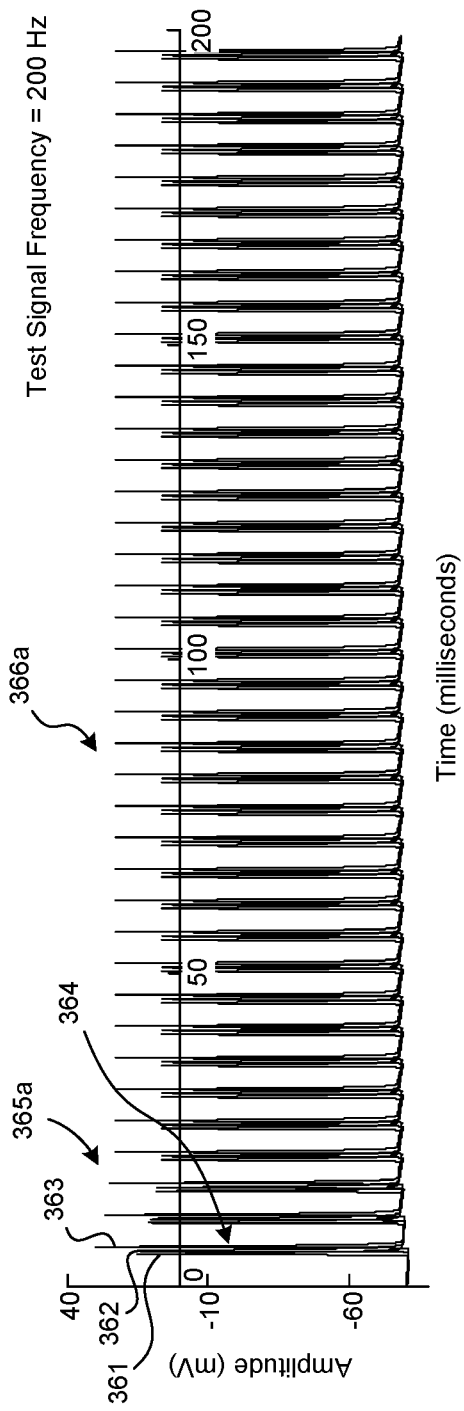
FIGS. 3A-3E are graphs illustrating response curves obtained from a computational simulation of neural responses to both test pulses and therapy signals at multiple frequency values, in accordance with embodiments of the present technology.

FIGS. 3A-3E illustrate the responses produced at the recording nodes shown in FIG. 2B, when signals of different frequencies were applied at the injection node 250. FIG. 3A illustrates the response curves for a test signal injected at the injection node 250 at a frequency of 200 Hz. The corresponding first, second, and third response curves 361, 362, and 363 are grouped closely together, and for purposes of illustration and discussion, are referred to as a composite response curve 364. The composite response curve 364 can include an initial response period 365a (immediately following the test pulse injection) and a subsequent response period 366a (at a later time). As shown in FIG. 3A, the responses of the neuron during the initial and subsequent response periods 365a, 366a were generally similar, and indicate that the neuron accurately tracked and transmitted signals injected at 200 Hz over the course of time.

Figure 3B:
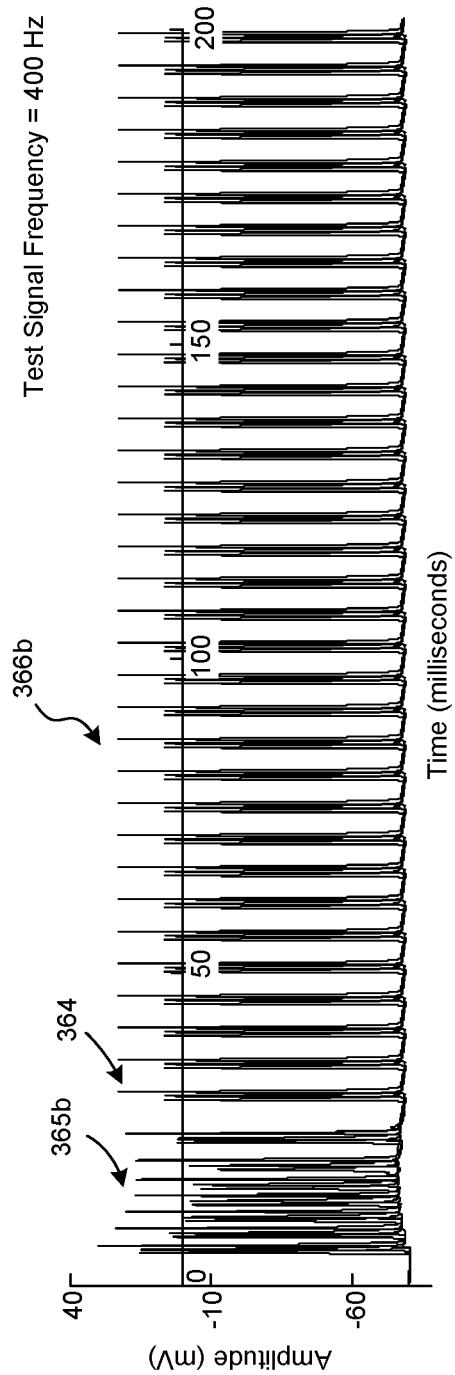

FIG. 3B illustrates the neural response when the frequency of the test signal applied at the injection node was increased to 400 Hz. As shown in FIG. 3B, during an initial response period 365b, the composite neural response curve 364 indicates that the neuron tracked the test signal at the increased frequency, and during a subsequent response period 366b, the neuron did not.

Figure 3C:
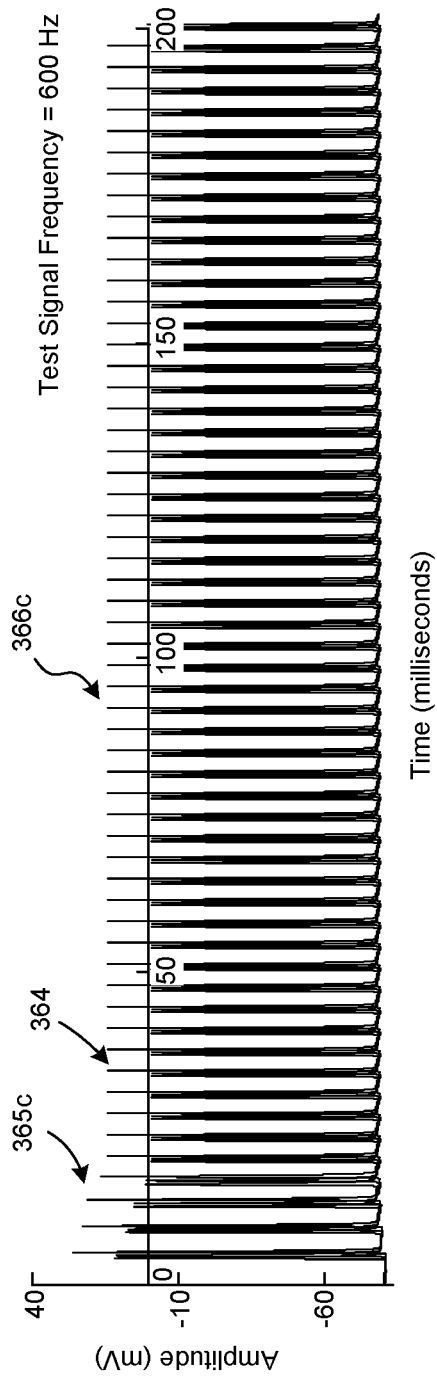

In FIG. 3C, the frequency of the test signal injected at the injection node 250 (FIG. 2B) was increased to 600 Hz. During both an initial response period 365c and a subsequent response period 366c, the neural responses were similar (as indicated by the generally uniform composite response curve 364), but during neither period did the neuron accurately track the rate at which the test pulses were injected at the injection node. In particular, while the test pulses were injected at a rate of 30 pulses during a 50 millisecond interval, the composite response curve 364 indicates a response rate of only about 15 pulses during a 50 millisecond interval.

Figure 3D:
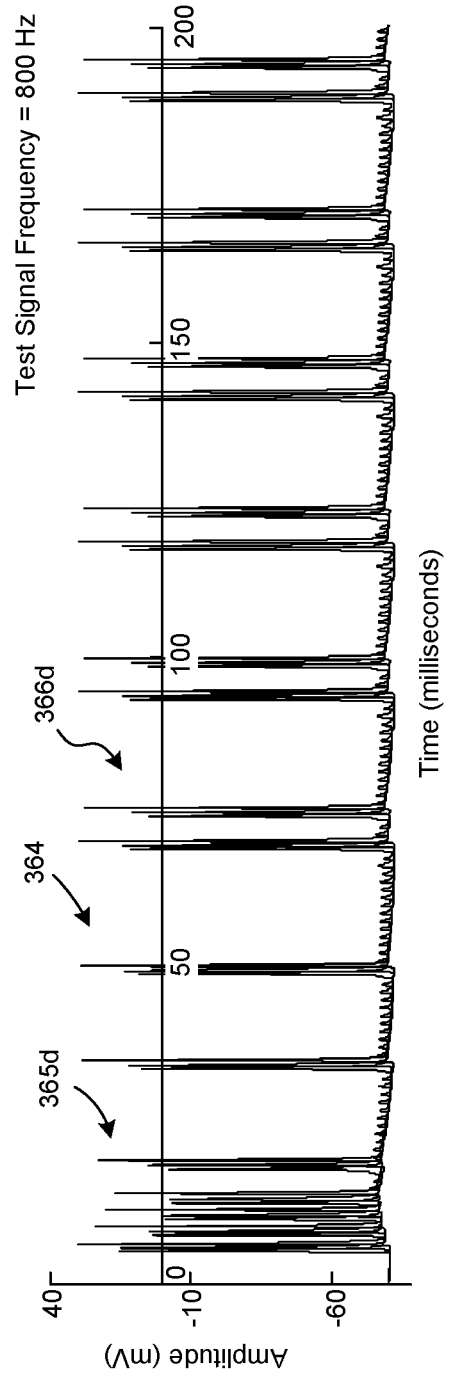
Figure 3E:
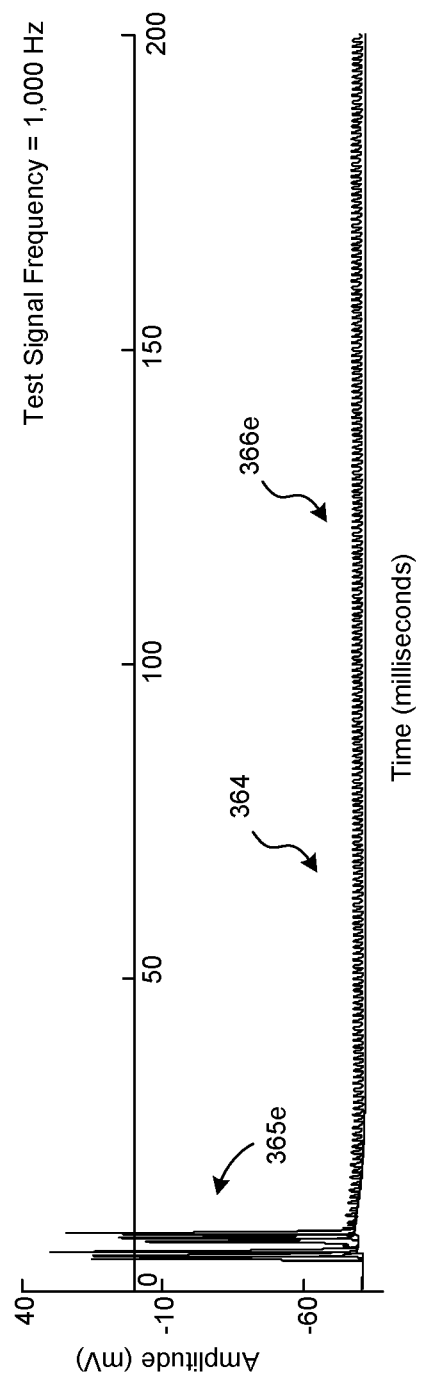

In FIG. 3D, the frequency of the signal at the injection node was increased to 800 Hz. The corresponding neural responses (as indicated by the composite response curve 364) during an initial response period 365d and a subsequent response period 366d illustrate that, again, the neuron failed to track the injected test pulses. In FIG. 3E, the frequency of the test signal was increased to 1 kHz and during a corresponding initial response period 365e and subsequent response period 366e, the neuron again failed to keep up with the injected test pulses.

Taken together, FIGS. 3A-3E illustrate that a degenerated neuron may be able to track pulses introduced at a relatively low frequency (e.g., 200 Hz or below), but is unable to accurately track pulses injected at higher frequencies. Such frequencies can occur naturally, particularly in neurons at the spinal cord, which receive inputs from multiple sources. FIGS. 3A-3E also illustrate that the response of the degenerated neuron appears not to be linear. In particular, the qualitative characteristics of the neuron's response change in a non-linear manner, as evidenced by the variations in the composite response curve 364 over FIGS. 3A-3E.

Figure 4:
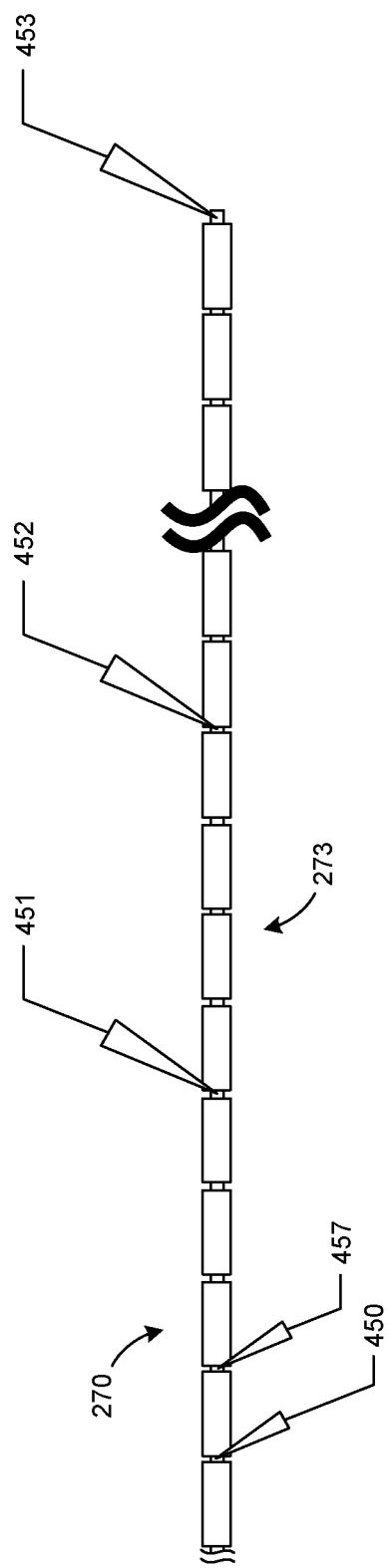
FIG. 4 schematically illustrates a simulated axon of a representative neuron in a computational model, identifying a test pulse injection node, therapy pulse injection node, and multiple recording nodes, in accordance with embodiments of the present technology.

FIG. 4 schematically illustrates a computationally simulated neuron 270, with a test pulse injection node 450 and a therapy pulse injection node 457. FIG. 4 also illustrates first and second recording nodes 451, 452, which are located at approximately the same distances from the test pulse injection node 450 as in the model shown in FIG. 2B and a third recording node 453 at the other end of the axon 273. Unlike the model shown in FIG. 2B, in the model illustrated in FIG. 4, a therapy signal is injected at the therapy pulse injection node 457. The following Figures illustrate the effect of the therapy signal on the ability of the neuron 270 to accurately transmit the test pulses injected at the test pulse injection node 450.

Figure 5A:
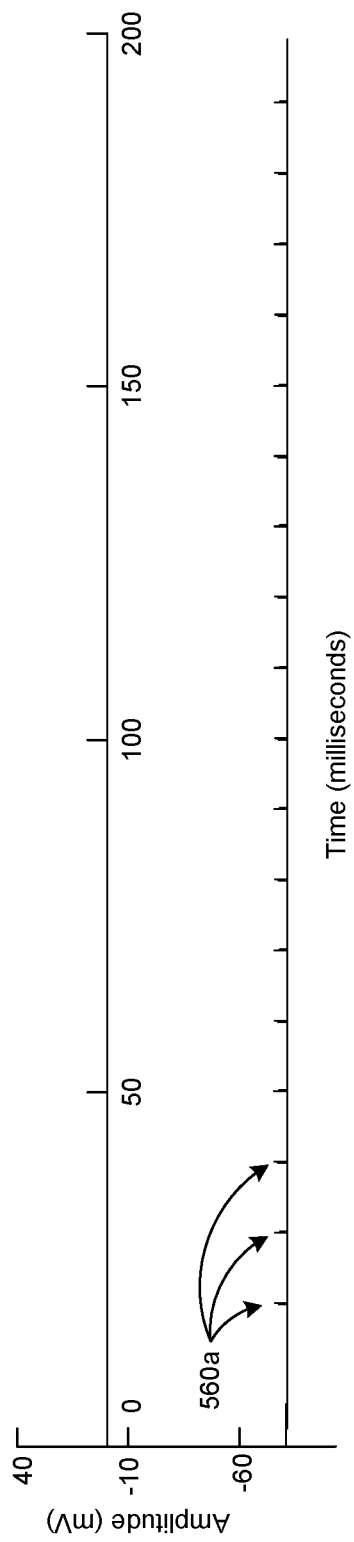

FIG. 5A illustrates a series of test pulses 560a applied at a frequency of 100 Hz, a pulse width of 100 microseconds, and an amplitude set at approximately 80% of the activation threshold of the neuron. Because the pulses were delivered at a subthreshold level, no response was recorded at any of the recording nodes shown in FIG. 4.

Figure 5B:
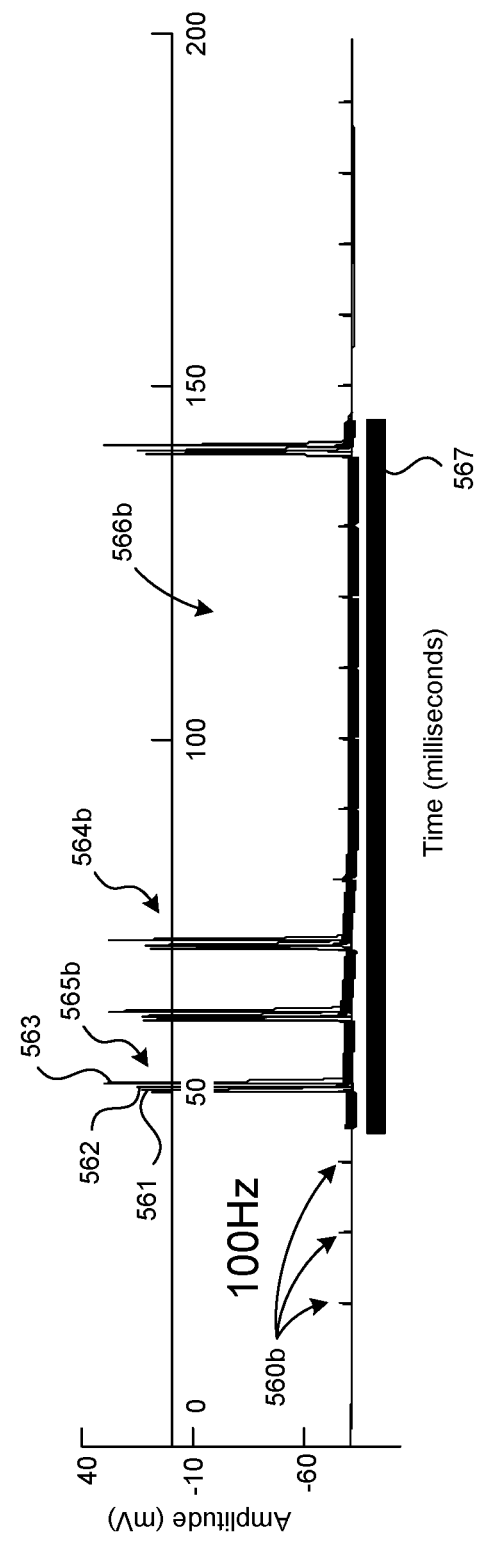

In FIG. 5B, test pulses 560b were again delivered at 100 Hz. In addition, therapy pulses 567 were delivered at a frequency of 10 kHz. As shown in FIG. 5B, the neuron produced responses (illustrated by first, second and third response curves 561, 562, 563 and a composite response curve 564b), over an initial response period 565b, and a subsequent response period 566b. As is evident from FIG. 5B, the neuron initially transmitted the 100 Hz test pulses, then failed to do so, and then began to transmit the pulses again.

FIG. 5C illustrates the simulated neural response when the frequency of the test pulses 560c was increased to 200 Hz. During the corresponding initial response period 565c, the neuron again tracked the injected test pulses (as indicated by the composite response curve 564c), and then during the subsequent response period 566c, failed to do so. When the frequency of the test pulses 560d was increased to 400 Hz (as shown in FIG. 5D) the neuron's performance (indicated by the composite response curve 564d) was nearly the same over corresponding initial and subsequent response periods 565d, 566d.

Figure 6A:
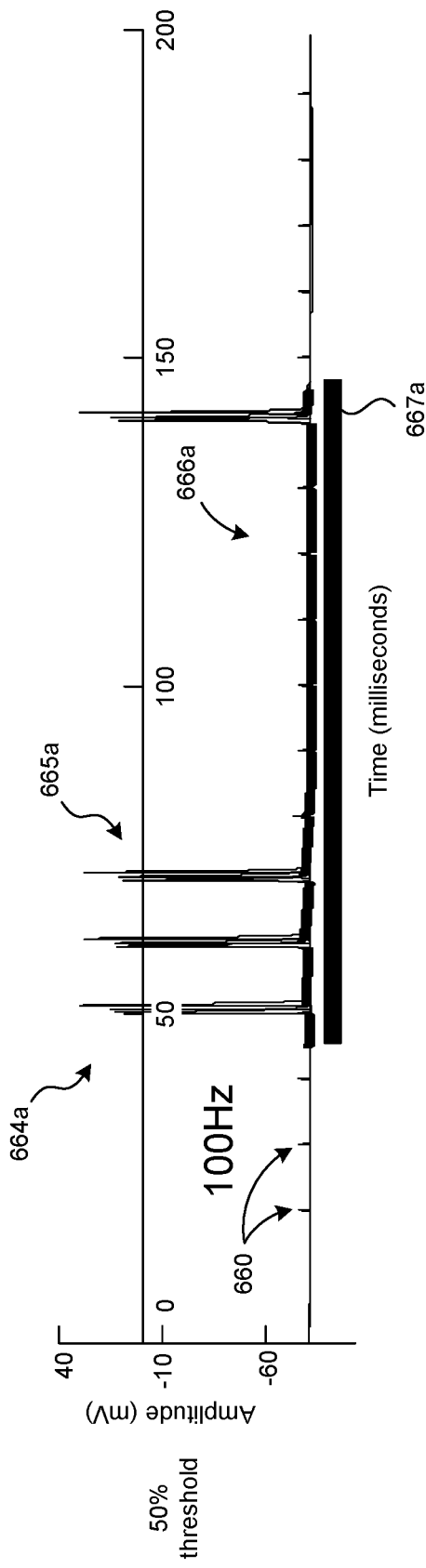
FIGS. 6A-6C illustrate representative response curves for test pulses injected at 100 Hz and therapy signals administered at multiple amplitudes in accordance with embodiments of the present technology.
Figure 6B:
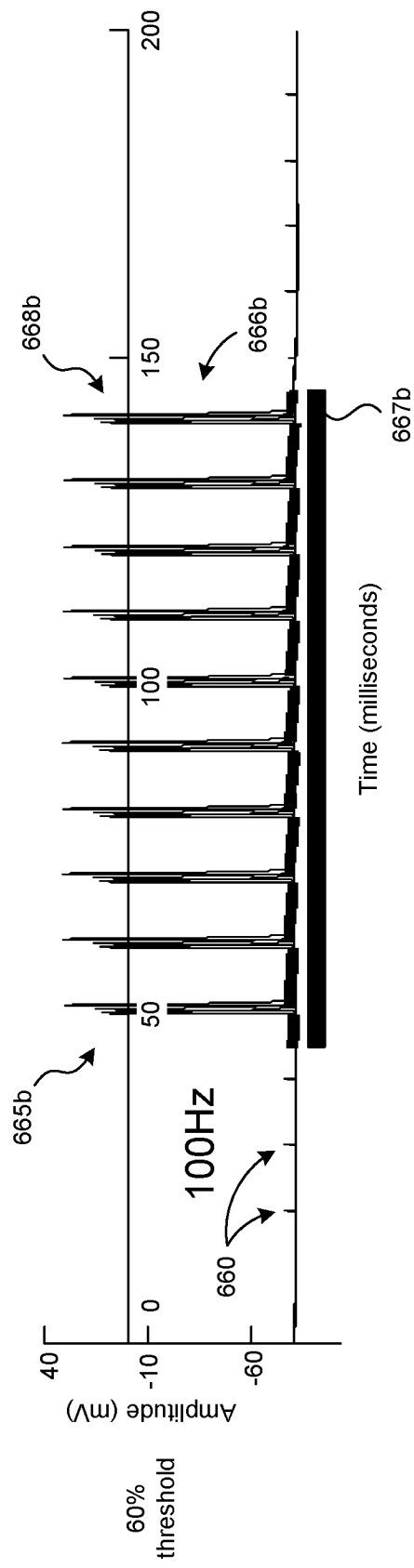
Figure 6C:
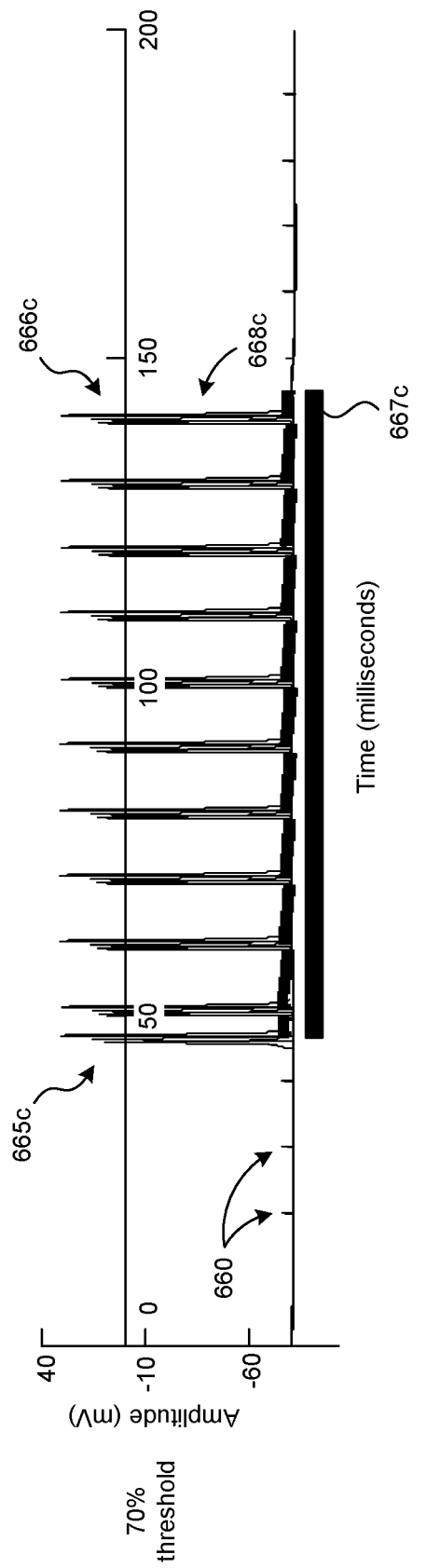

The foregoing results were performed with the therapy pulses delivered at a frequency of 10 kHz and an amplitude set at 50% of the activation threshold for a 100 Hz signal. FIGS. 6A-6C illustrate the result when the amplitude of the therapy signal was increased. In FIG. 6A, the amplitude of the therapy signal 667a was set at the baseline level of 50% of threshold, and accordingly, during an initial response period 665a and a subsequent response period 666a, the composite response curve 664a matches the corresponding composite response curve 564b described above with reference to FIG. 5B. In FIG. 6B, the amplitude of the therapy signal 667b was increased to 60% of threshold. The response of the neuron was to produce a continuous composite response curve 668b, illustrating that the neuron accurately tracked the injected test pulses, both during an initial response period 665b and during a subsequent response period 666b. When the amplitude of the therapy signal 667c was further increased to 70% of threshold (as shown in FIG. 6C) the corresponding continuous composite response curve 668c generally followed the injected test pulses 660, but did so less accurately during an initial period 665c than during a subsequent period 666c. Based on this simulation, it is believed that delivering the therapy signal at an amplitude that is too close to the neuron's threshold amplitude may not produce accurate responses in the neuron.

Figure 7A:
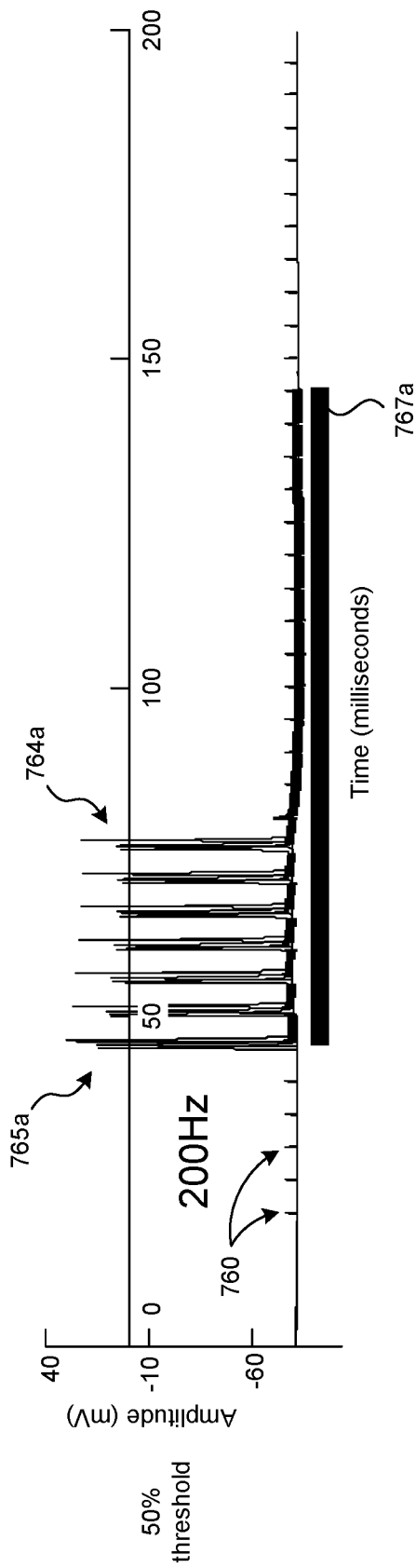
FIGS. 7A-7B illustrate response curves for test pulses injected at 200 Hz and therapy signals administered at multiple amplitudes in accordance with embodiments of the present technology.
Figure 7B:
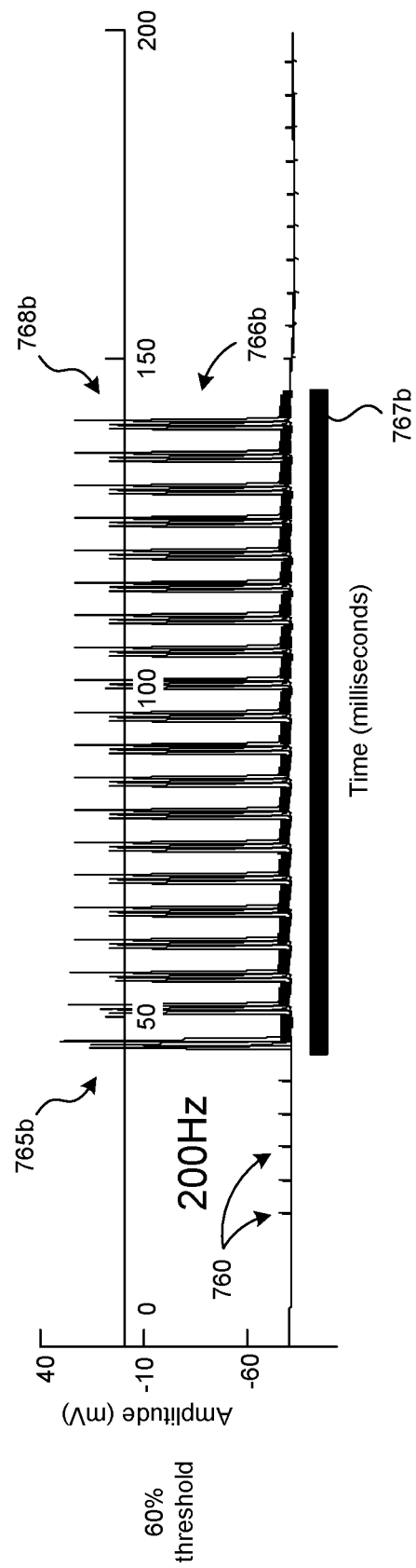

FIGS. 7A and 7B illustrate the effect of increasing the amplitude of the therapy signal when the test pulses 760 were injected at a frequency of 200 Hz rather than 100 Hz. As shown in FIG. 7A, when a therapy signal 767a was delivered at 50% of threshold, the neuron produced a composite response curve 764a, that did not sustain an accurate tracking of the test pulses 760 beyond an initial response period 765a. As shown in FIG. 7B, when the amplitude of a therapy signal 767b was increased to 60% of threshold, the neuron produced a corresponding continuous composite response curve 768b, accurately tracking the injected test impulses 760 over both an initial response period 765b and a subsequent response period 766b.

Figure 8A:
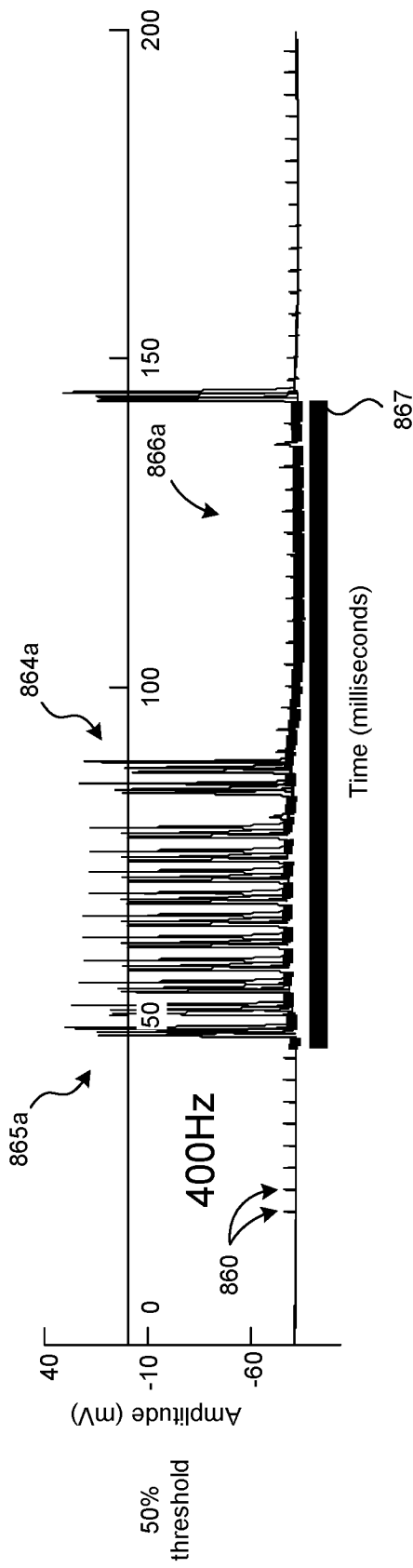
FIGS. 8A-8B illustrate response curves corresponding to test pulses injected at 400 Hz and therapy signals administered at multiple amplitudes in accordance with embodiments of the present technology.
Figure 8B:
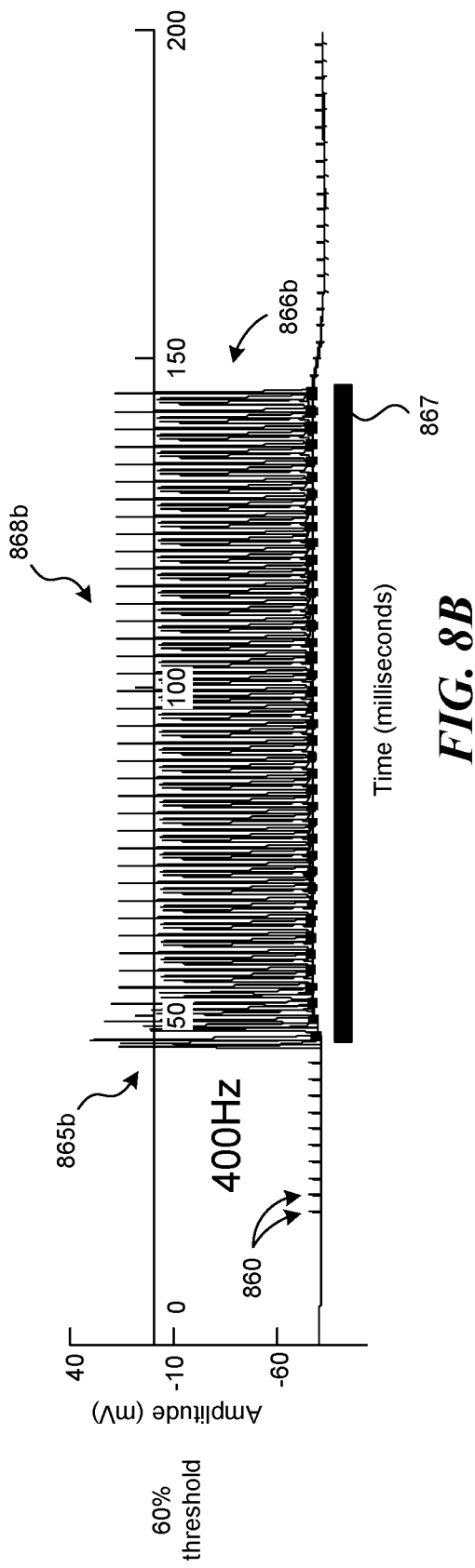

A similar effect was observed when the pulses were injected at 400 Hz and the therapy signal 867 was delivered at 10 kHz and 50% of threshold, as shown in FIGS. 8A and 8B. In FIG. 8A, the neuron produced a composite response curve 864a that does not track each injected test pulse 860 during an initial period 865a, and fails to track nearly all injected test pulses 860 during a subsequent response period 866a. As shown in FIG. 8B, when the amplitude of therapy signal 867 was increased to 60% of threshold, the neuron produced a continuous composite response curve 868b, accurately tracking each injected test pulse over both an initial response period 865b and a subsequent response period 866b.

Figure 9A:
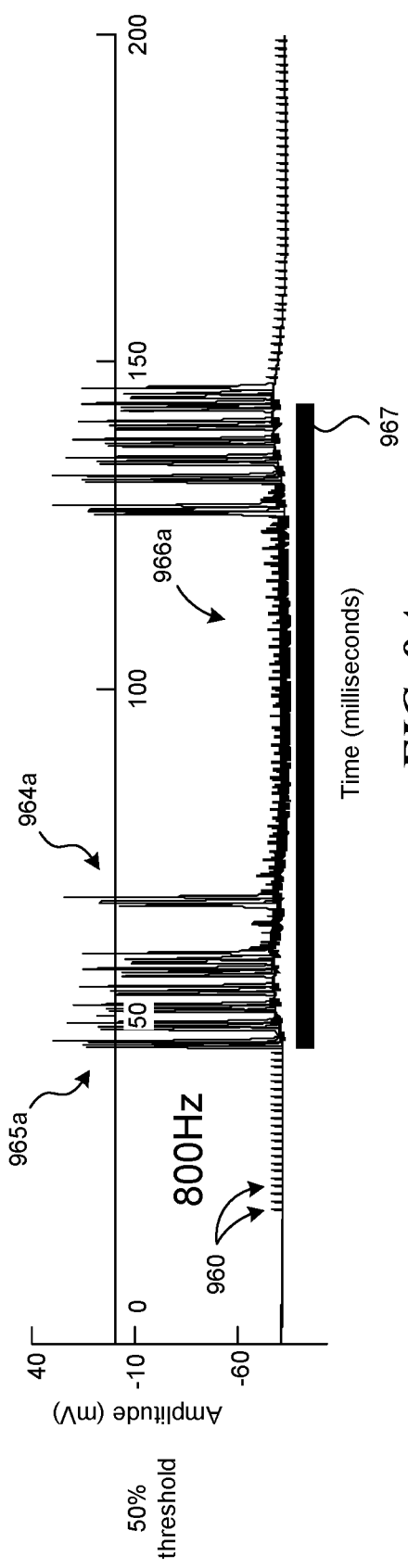
FIGS. 9A-9C illustrate response curves corresponding to test pulses injected at 800 Hz and therapy signals administered at multiple amplitudes and frequencies in accordance with embodiments of the present technology.
Figure 9B:
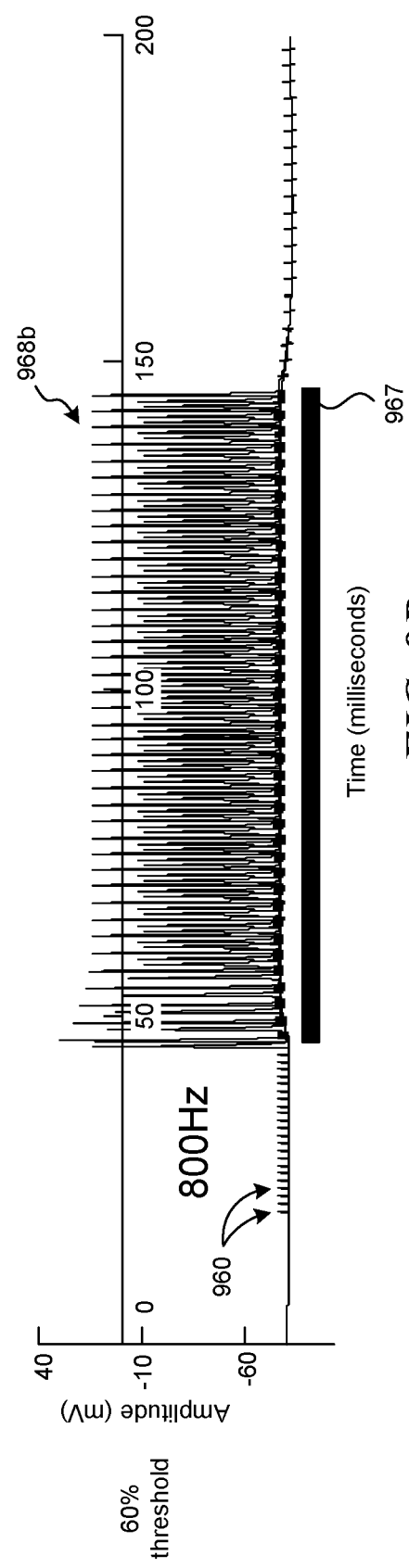
Figure 9C:
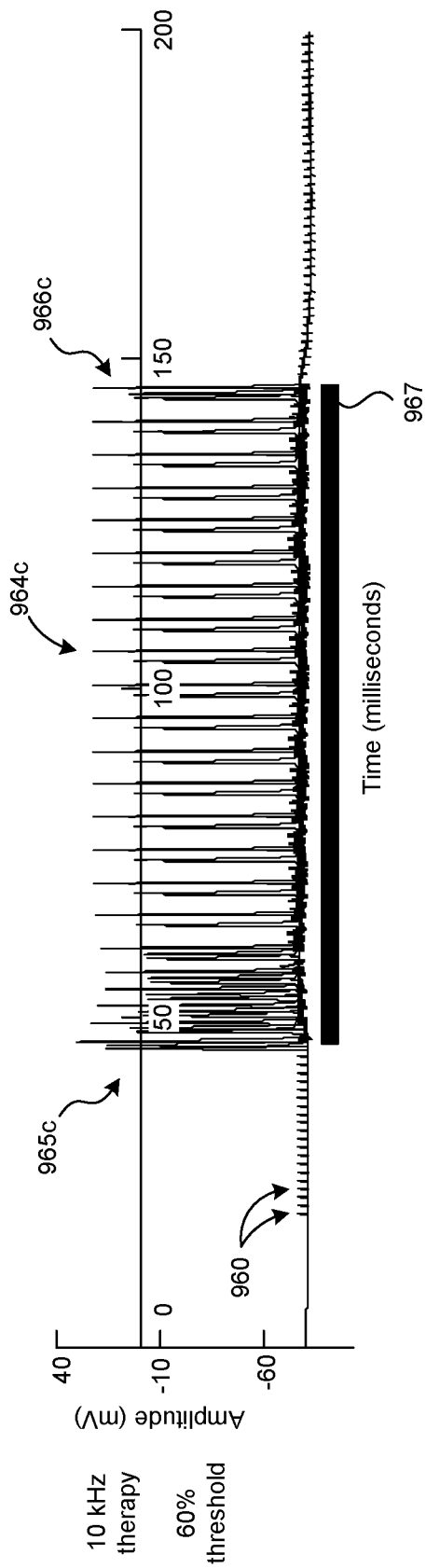

FIGS. 6A-8B, discussed above, illustrate the effect of therapy signal amplitude, at a frequency of 10 kHz, on the ability of the neuron to accurately transmit injected test pulses. FIGS. 9A-9C illustrate the effect of therapy signal amplitude at different frequencies. FIG. 9A graphically illustrates test pulses 960 injected at a frequency of 800 Hz, and the corresponding composite response curve 964a (over initial and subsequent response periods 965a, 966a) when the therapy signal 967 was provided at 50% of threshold. FIG. 9B illustrates the result when the amplitude of the therapy signal 967 was increased to 60% of threshold, producing a continuous composite response curve 968b, generally similar to the continuous composite response curves described above with reference to FIGS. 6A-8B.

FIG. 9C illustrates the neural response when the frequency of the therapy signal 967 was reduced from 10 kHz to 5 kHz, with the amplitude maintained at 60% of threshold. As shown by the composite response curve 964c, the neuron accurately tracked the injected test pulses during an initial period 965c, but failed to do so during a subsequent period 966c. This simulated result illustrates that reducing the frequency of the therapy signal has an effect on the ability of the neuron to accurately track the injected test pulses 960, with all other parameters held constant. It is expected that adjusting other parameters (for example, signal amplitude) may produce a greater beneficial effect than is shown in FIG. 9C, and, in at least some embodiments, a beneficial effect equivalent to that shown in FIG. 9B.

Based on the foregoing results, it is expected that the high frequency therapy signal can allow naturally-occurring signals (that are otherwise subthreshold) to trigger an action potential and be transmitted along the axon of the neuron. It is further believed that one aspect of neural degeneration in the patient is that neural signals that are normally suprathreshold are instead subthreshold. One potential application of this approach is based on an understanding that, in a degenerative large fiber neuron, normal sensory signal traffic is inhibited (e.g., because the signals are subthreshold rather than suprathreshold). As a result, pain signals (which are transmitted along smaller fibers), may dominate the sensory input received by the patient. Preclinical data has shown that the conduction velocity and refractory period changed in neuropathic animals. See, e.g., Zhu, et al., *Early Demyelination of Primary A-Fibers Induced a Rapid-Onset of Neuropathic Pain in Rat* (2012); Zhu, et al., *Changes in Functional Properties of A-Type But Not C-Type Sensory Neurons In Vivo In a Rat Model of Peripheral Neuropathy* (2012); Zhu, et al., *Excitability of AB Sensory Neurons is Altered In an Animal Model of Peripheral Neuropathy* (2012); and Lachance, et al., *Stimulation-Induced Ectopicity and Propagation Windows In Model Damaged Axons* (2014). A recent clinical QST study showed that patients with polyneuropathy displayed loss of sensory functions (http://www.ncbi.nlm.nih.gov/pubmed/26630440). On the other hand, if the patient receives more normal sensory inputs (e.g., as indicated by the continuous composite response curves described above), the dominating effect of the pain signals may be reduced or eliminated.

Based on the foregoing results, it is expected that directing a high frequency therapy signal to the axon of a degenerative neuron can perform one or more of the following functions. First, the signal can rehabilitate the neuron's ability to accurately transmit the naturally occurring signals it receives. Second, it is expected that a patient's ability to respond to a high frequency therapy signal may be evaluated by determining the effect of the high frequency signal on the patient's sensory threshold. In particular, one effect of the high frequency therapy signal appears to be that it allows transmission of signal traffic that is otherwise inhibited. When such signal traffic is inhibited, the patient fails to receive the sensory inputs. Accordingly, the effect of the high frequency therapy may be to allow the patient to feel sensations that the patient previously could not. In particular embodiments, this effect can be used to screen patients who are likely to respond to high frequency stimulation from those who are not. In other embodiments, this technique can be used to adjust the parameters of a therapy signal applied to a patient who is already receiving high frequency stimulation. Further details of representative screening and adjustment techniques are described below.

A representative screening technique can be applied as part of the typical trial (discussed above under Heading 1.0) to reduce the amount of time required to determine whether or not the patient is likely to respond to a high frequency therapy. In particular, the patient's response to the foregoing sensitivity test is expected to be quicker than (but still indicative of) the patient's response to electrical therapy directed to treat chronic pain. Accordingly, the time required to identify patients likely to achieve a successful outcome with a permanent implant can be reduced, e.g., from days to minutes. In at least some embodiments, this process can also significantly reduce the time required to identify stimulation parameters (e.g., active electrode combinations, stimulation location, frequency, pulse width, duty cycle, amplitude and/or waveform) for the patient. A successful outcome in this context means identifying the patient as a suitable candidate for an implanted high frequency therapy system. In particular embodiments, the successful outcome can also include identifying stimulation parameters (e.g., optimum stimulation parameters in at least some cases) for use with the implanted high frequency therapy system.

Figure 10:
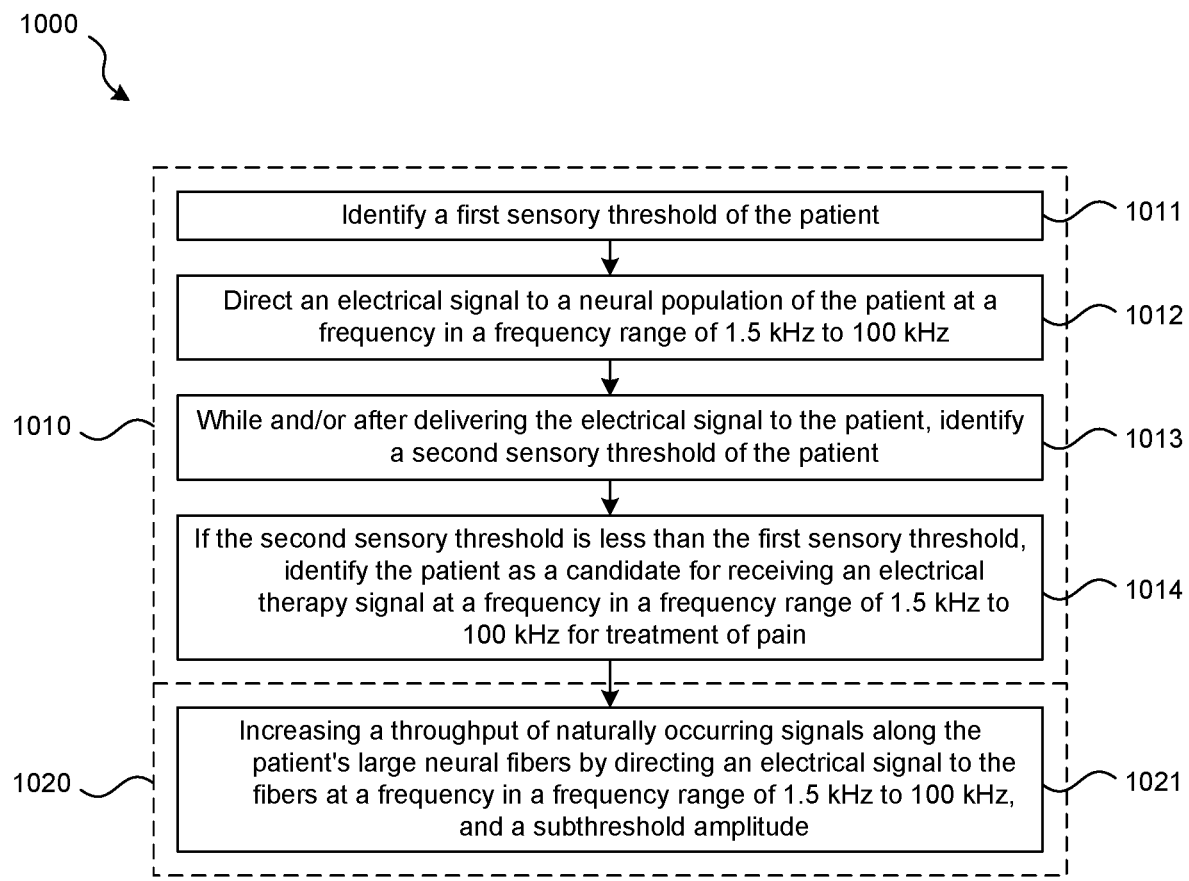
FIG. 10 illustrates a flow diagram for carrying out multiple methods in accordance with embodiments of the present technology.
Figure 11:
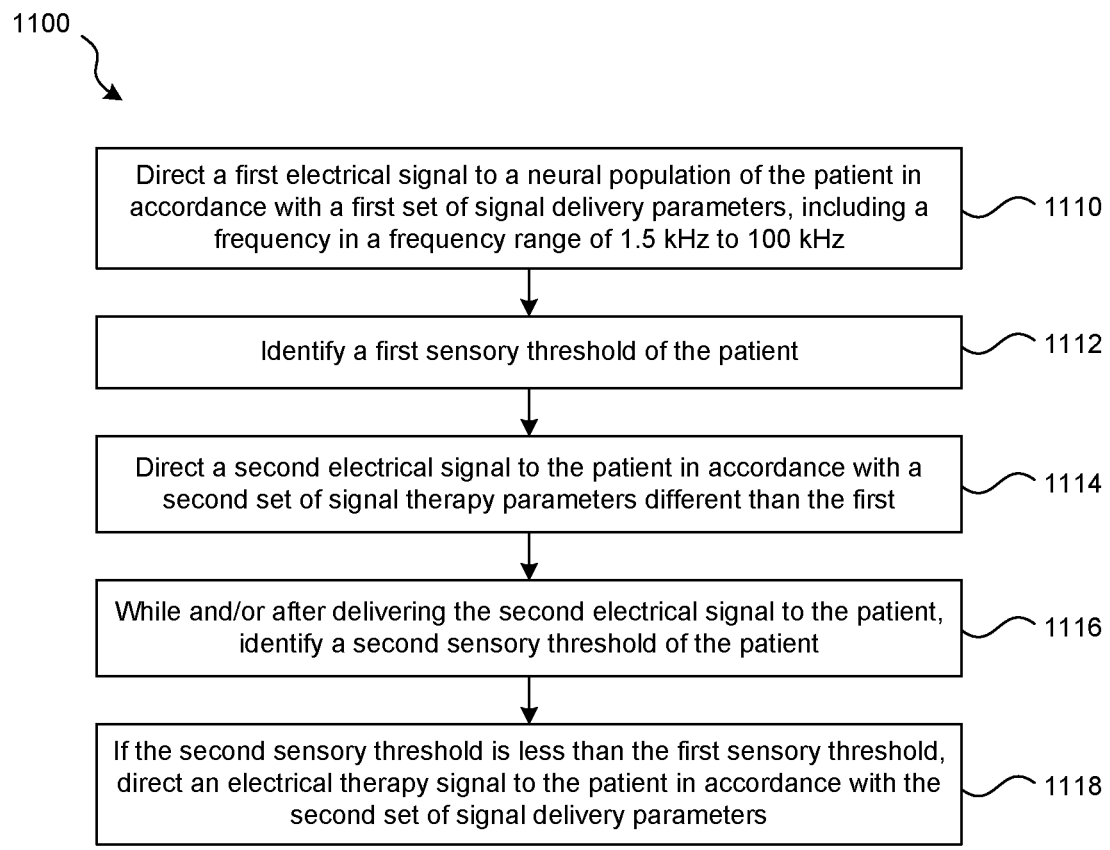
FIG. 11 illustrates a flow diagram for carrying out multiple methods in accordance with further embodiments of the present technology.

FIG. 10 illustrates a method for both identifying a potentially responsive patient, and administering a therapy to a responsive patient. FIG. 10 illustrates a representative process 1000 that includes an identification phase 1010 and a therapy phase 1020 which can be performed independently of one another, or successively. In the identification phase 1010, the process 1000 can include identifying a first (e.g., baseline) sensory threshold of the patient (block 1011). This process can include testing the patient's sensitivity to any suitable sensory input, e.g., a pin prick, pressure, heat, and/or cold. In other embodiments, the sensory input can be an electrical signal delivered from a skin-mounted electrode (e.g., a TENS electrode) so as to limit the invasiveness of the screening process. When an electrical signal is used to deliver the stimulus (sometimes referred to herein as a sensory stimulation signal), the parameters of the signal can be different than those of the therapy signal. For example, the sensory stimulation signal can have a frequency below 1.5 kHz rather than at or above 1.5 kHz. In a particular embodiment, the sensory stimulation signal can have a frequency of 1 Hz. In addition (and unlike a non-paresthesia-generating high frequency therapy signal), the amplitude of the sensory stimulation signal can be deliberately ramped up to be suprathreshold, so as produce a sensory response, in order to establish the patient's sensory threshold. In still further embodiments, the sensory input can be delivered by an implanted signal delivery device (e.g., a percutaneous lead or other temporarily or permanently implanted device). In any of these embodiments, the sensory input corresponds to the test pulses of the simulations described above. The process further includes directing an electrical signal to a neural population of the patient at a frequency in a frequency range of 1.5 kHz to 100 kHz (block 1012). If the patient already has an implanted electrode (e.g., an SCS electrode), the signal can be delivered to the already-implanted electrode, as described above. If the patient does not have an implanted lead or other signal delivery device, the method can include implanting such a signal delivery device as part of the screening process.

While (and/or after) delivering the electrical signal to the patient, the process 1000 can include identifying a second sensory threshold of the patient (block 1013). If the second sensory threshold is less than the first sensory threshold, the process 1000 can include identifying the patient as a candidate for receiving an electrical signal (e.g., an electrical therapy signal) at a frequency in a frequency range of 1.5 kHz to 100 kHz for treatment of pain and/or another disorder (block 1014). Once a suitable candidate has been identified using the foregoing technique, the patient's pain (or other disorder) can be addressed by applying the therapy signal, as indicated in phase 1020. Phase 1020 can include providing the patient with a therapeutic benefit via an electrical signal (e.g., an electrical therapy signal). For example, phase 1020 can include increasing a throughput of naturally occurring signals along the patient's large neural fibers by applying an electrical signal to the fibers at a frequency in a frequency range of 1.5 kHz to 100 kHz, at a subthreshold amplitude (block 1021). A particular practitioner may perform only phase 1010, only phase 1020, or both phases 1010 and 1020 on any given patient, depending, for example, on the characteristics of the patient and/or prior treatments the patient may have received.

In still further embodiments, techniques in accordance with the presently disclosed technology can be used to adjust the parameters of an electrical therapy signal delivered to the patient, in a manner that can significantly reduce the time required to identify suitable and/or improved parameters for the associated therapy. This process can be used for patients who are already receiving a high frequency electrical therapy signal, but for whom the therapy is not as effective as it can be, or has ceased to be effective. For example, referring now to FIG. 11, a representative process 1100 can include directing a first electrical signal to a neural population of the patient in accordance with a first set of signal delivery parameters, including a frequency in a frequency range of 1.5 kHz to 100 kHz (block 1110). Accordingly, block 1110 can refer to a patient receiving a high frequency therapy to address pain or another indication.

The process 1100 can further include identifying a first sensory threshold of the patient (block 1112) e.g., using any of the techniques described above with reference to block 1011. Because the patient is already receiving a high frequency electrical therapy signal, the device used to deliver the therapy signal can also be used to deliver a sensory stimulation signal. For example, an existing implanted signal delivery device can be used to deliver the sensory stimulation signal. In other embodiments, another device (e.g., a TENS device) can be used to deliver the sensory stimulation signal.

The process 1100 can further include changing the electrical therapy signal applied to the patient, for example, if the patient is no longer receiving a therapeutic benefit from the first electrical signal, or if it is expected that the patient can receive additional benefit from an electrical signal having different parameters. Accordingly, the process can include directing a second electrical signal to the patient in accordance with a second set of signal delivery parameters different than the first (block 1114). As used in the context of block 1114, the "different" means that any one parameter in accordance with which the second electrical signal is delivered is different than a corresponding parameter in accordance with which the first electrical signal was delivered. For example, the second electrical signal can have a different amplitude, a different pulse width, a different frequency, a different duty cycle, and/or a different delivery location than that of the first electrical signal.

At block 1116, the process 1100 includes identifying a second sensory threshold of the patient, while (and/or after) delivering the second electrical signal to the patient. For example, block 1116 can correspond generally to block 1013 described above. If the second sensory threshold is less than the first sensory threshold, the process can include directing an electrical therapy signal to the patient in accordance with the second set of signal delivery parameters (block 1118). Accordingly, as was discussed above in the context of the screening process shown in FIG. 10, the process shown in FIG. 11 can shorten the time required to identify new stimulation parameters by using a real-time or near real-time change in the patient's sensory threshold, rather than waiting (what is typically a longer period of time) for the patient to exhibit a reduction in pain or other therapeutic response.

Figure 12:
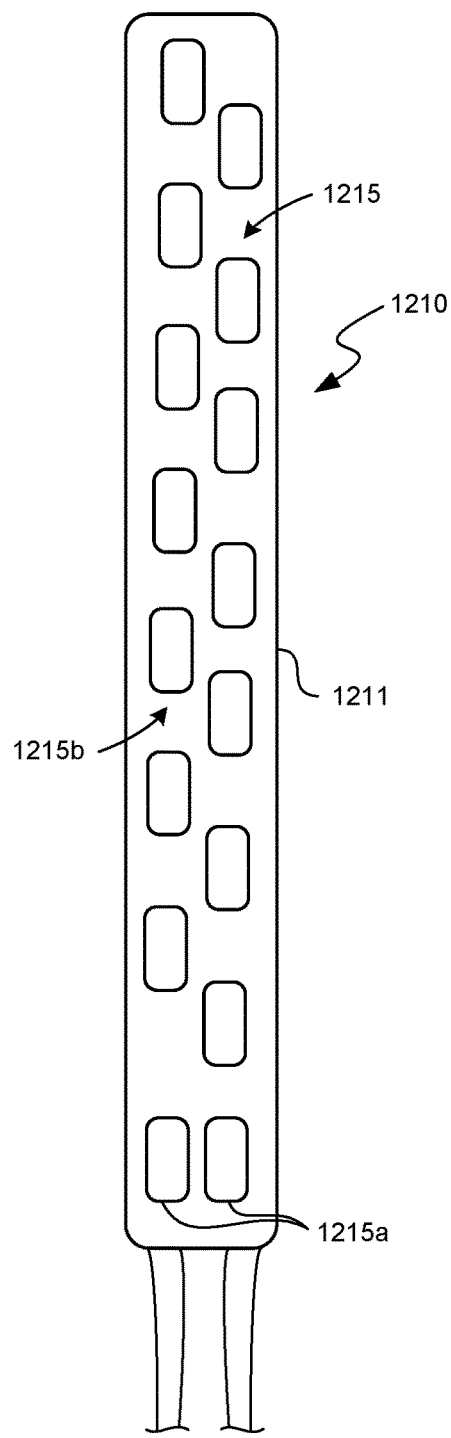
FIG. 12 illustrates a paddle-type signal delivery device configured to deliver signals to a patient in accordance with an embodiment of the present technology.

FIG. 12 is a partially schematic illustration of a representative signal delivery device 1210 suitable for delivering therapy signals and/or other electrical signals (e.g., test signals or sensory stimulation signals) to the patient. In a particular aspect of this embodiment, the signal delivery device 1210 can have a paddle-type configuration, and can accordingly include a paddle body 1211 having multiple signal delivery contacts 1215. In a particular aspect of this embodiment, the signal delivery contacts 1215 can include one or more contacts that are selected to deliver sensory stimulation signals (e.g., to determine the patient's sensory threshold) and one or more contacts selected to deliver an electrical therapy signal (e.g., to provide a therapeutic benefit to the patient). For example, a pair of first contacts 1215*a* can be used to deliver sensory stimulation signals, and any of the remaining second contacts 1215*b* can be used to apply a therapy signal to the patient. In general, the first contacts 1215*a* are different than the second contacts so as to avoid overlapping the effects of the sensory stimulation signal and a (potentially) therapeutic signal. However, in at least some embodiments, the same contact(s) can be used to deliver the sensory stimulation signals and the therapy signals.

Figure 13:
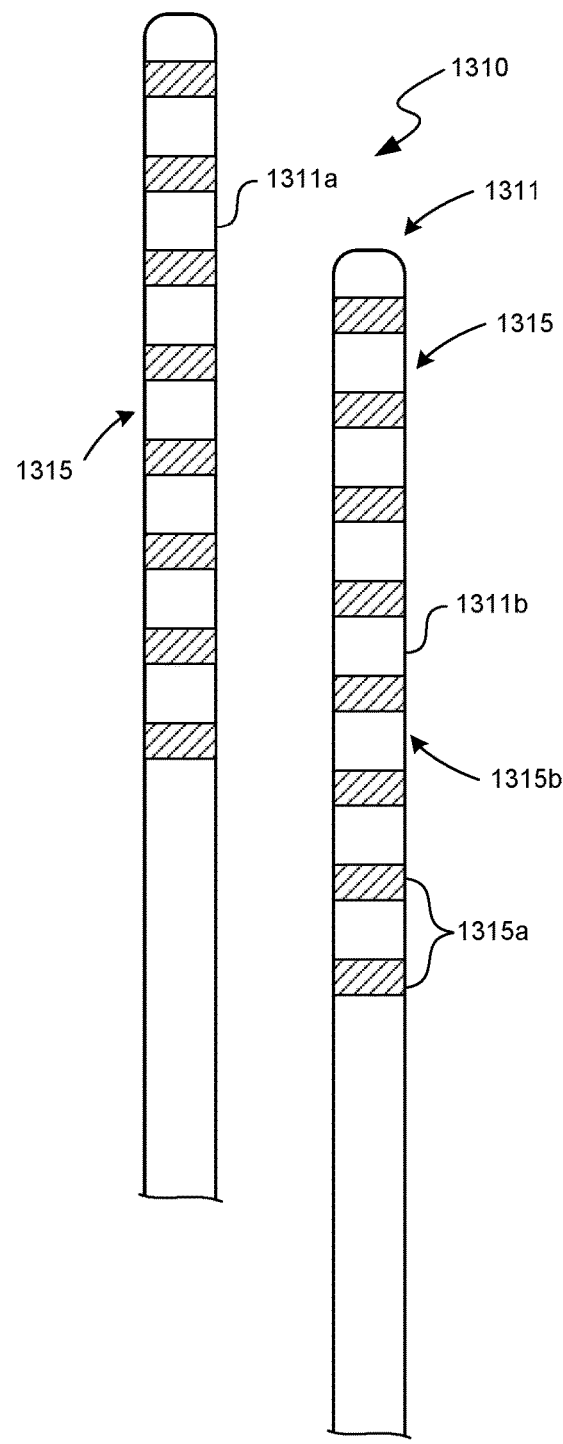
FIG. 13 illustrates percutaneous signal devices configured to deliver signals to a patient in accordance with an embodiment of the present technology.

In other embodiments, the signal delivery device can have other configurations, for example, configurations similar to those described above with reference to FIGS. 1A and 1B. FIG. 13 illustrates a representative pair of signal delivery devices 1310, including a first lead or lead body 1311*a*, and a second lead or lead body 1311*b*. The lead or leads 1311 can include multiple signal delivery contacts 1315, and, in a manner generally similar to that discussed above, the signal delivery contacts 1315 can include first signal delivery contacts 1315*a* used to deliver sensory stimulation signals, and second signal delivery contacts 1315*b* used to deliver therapy signals.

Figure 14:
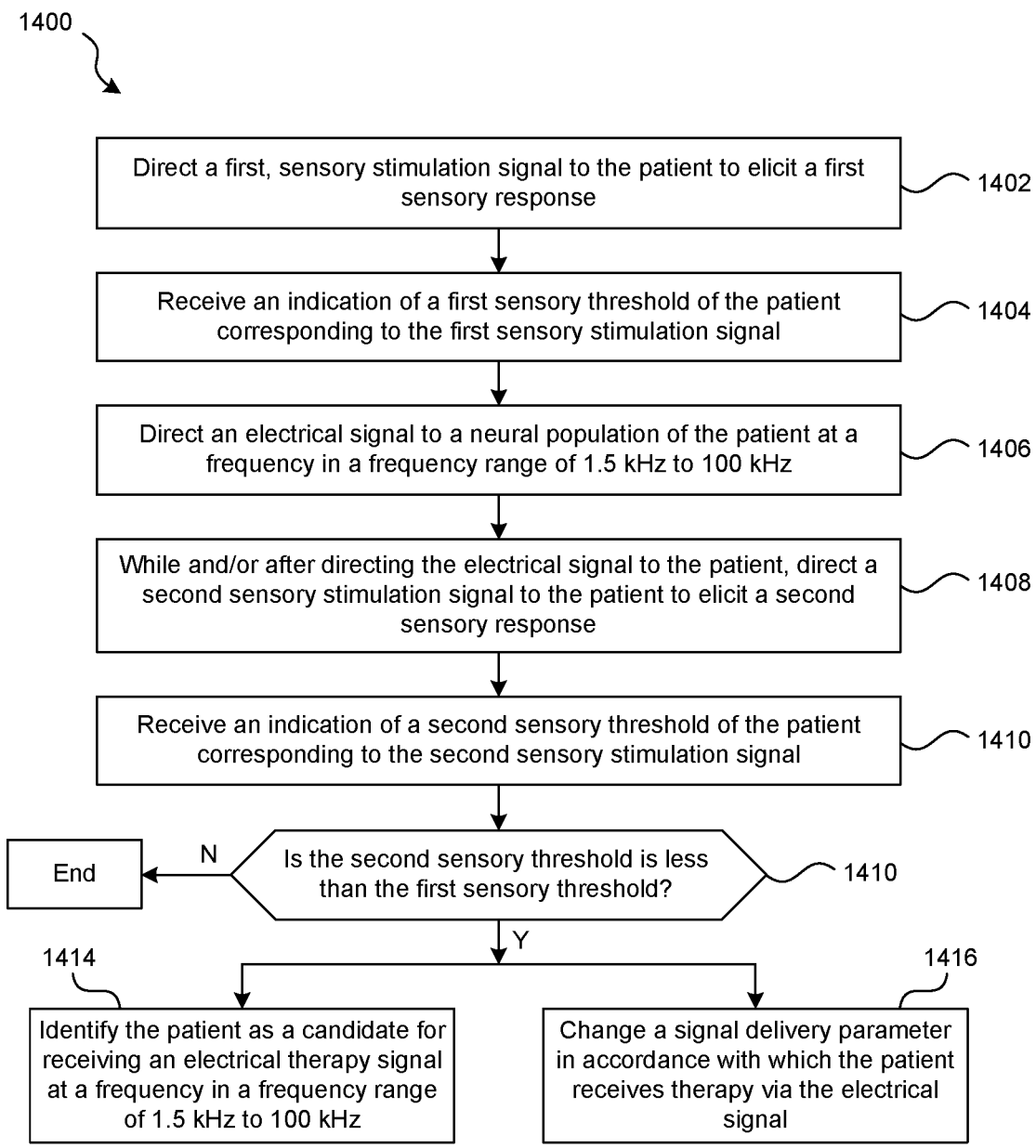
FIG. 14 illustrates a flow diagram for carrying out multiple methods in accordance with still further embodiments of the present technology.

The signal delivery devices discussed above with reference to FIGS. 12 and 13 (or other types of signal delivery devices) can be coupled to a signal generator for patient treatment and/or screening. A representative system (to which the signal delivery devices can be connected) includes a signal generator that in turn includes signal generation circuitry, for example, as described above with reference to FIG. 1A. The system can further include a computer readable medium operatively coupled to the signal generation circuitry and programmed with instructions. As shown in FIG. 14, the instructions can perform a process 1400. At block 1402, the process 1400 can include directing a first, sensory stimulation signal to the patient to elicit a first sensory response. At block 1404, the process can include receiving an indication of a first sensory threshold of the patient corresponding to the first sensory stimulation signal. For example, the amplitude of the first sensory stimulation signal can be increased until it triggers a sensory response in the patient, which corresponds to the first sensory threshold, and which may be entered into the system by the patient or a practitioner, or determined automatically (e.g., when the patient or practitioner ceases increasing the signal amplitude).

The process can further include directing an electrical signal to a neural population of the patient at a frequency in a frequency range of 1.5 kHz to 100 kHz (block 1406). At block 1408, the process includes directing a second sensory stimulation signal to the patient to elicit a second sensory response, while (and/or after) directing the electrical signal to the patient. Block 1410 includes receiving an indication of a second sensory threshold of the patient corresponding to the second sensory stimulation signal. The indication can be received in any of the manners described above with reference to block 1404.

At block 1412, the process includes determining whether the second sensory threshold is less than the first sensory threshold. If it is, the process can continue to block 1414 or block 1416. Block 1414 includes identifying the patient as a candidate for receiving an electrical therapy signal at a frequency in a frequency range of 1.5 kHz to 100 kHz, in response to the indication that the second sensory threshold is less than the first. At block 1416, the process can include changing a signal delivery parameter in accordance with which the patient receives therapy via the electrical signal. Accordingly, block 1414 corresponds to using the results of the sensory stimulation process to screen the patient, and block 1416 includes using the results to adjust the patient's therapy parameters.

3.0 Additional Embodiments

As described above, in representative embodiments, the patient may receive high frequency therapeutic signals with at least a portion of the therapy signal at a frequency from about 1.5 kHz to about 100 kHz, or from about 1.5 kHz to about 50 kHz, or from about 3 kHz to about 20 kHz, or from about 5 kHz to about 15 kHz, or from about 1.5 kHz to about 10 kHz, or at frequencies of about 8 kHz, 9 kHz, or 10 kHz.

In particular embodiments, representative current amplitudes for the therapy signal are from 0.1 mA to 20 mA, or 0.5 mA to 10 mA, or 0.5 mA to 7 mA, or 0.5 mA to 5 mA. Representative pulse widths range from about 10 microseconds to about 333 microseconds, about 10 microseconds to about 166 microseconds, 20 microseconds to about 100 microseconds, 30 microseconds to about 100 microseconds, and 30 microseconds to about 40 microseconds. Duty cycles can range from about 10% to about 100%, and in a particular duty cycle, signals are delivered for 20 seconds and interrupted for 2 minutes (an approximately 14% duty cycle). In other embodiments, these parameters can have other suitable values.

A method for treating a patient in accordance with a particular embodiment of the present technology includes increasing a throughput of naturally occurring signals along the patient's large neural fibers by applying an electrical signal to the fibers at a frequency in a frequency range of 1.5 kHz to 100 kHz, and a subthreshold amplitude. In further particular embodiments, the large fibers can include A fibers, but not C fibers. In further particular embodiments, the threshold amplitude is below the patient's sensory threshold. The fibers can be peripheral nerve fibers, and/or can be located at the patient's spinal cord. In particular embodiments, the signal is applied to the axons.

Another representative embodiment includes a method for identifying a patient as a candidate for pain treatment. The method can include identifying a first sensory threshold of the patient, directing an electrical signal to a neural population of the patient at a frequency in a frequency range of 1.5 kHz to 100 kHz, and identifying a second sensory threshold of the patient, while or after directing the electrical signal to the patient. If the second sensory threshold is less than the first sensory threshold, the method can include identifying the patient as a candidate for receiving an electrical therapy signal at a frequency in a frequency range of 1.5 kHz to 100 kHz, for example, to treat pain.

In further particular embodiments, the first sensory threshold can be identified by applying a test signal via an implanted device, e.g. to a peripheral nerve of the patient, or to the patient's spinal cord. In other embodiments, the test signal can be applied to the patient's skin. In still further embodiments, the method can be directed to adjusting an existing patient therapy regimen. For example, a representative method can include directing a first electrical signal to a neural population of the patient in accordance with a first set of signal delivery parameters, including a frequency in a frequency range of 1.5 kHz to 100 kHz. The method can further include identifying a first sensory threshold of the patient, and directing a second electrical signal to the patient in accordance with a second set of signal delivery parameters different than the first. The method can still further include identifying a second sensory threshold of the patient, while or after delivering the second electrical signal to the patient. If the second sensory threshold is less than the first, the method can include directing an electrical therapy signal to the patient in accordance with the second set of signal delivery parameters.

In still further embodiments, the technology includes systems for treating a patient. A representative system includes a signal generator that in turn includes signal generation circuitry and a computer readable medium. The computer readable medium is operatively coupled to the signal generation circuitry and is programmed with instructions that when executed direct a first, sensory stimulation signal to the patient to elicit a first sensory response, and receive an indication of a first sensory threshold of the patient corresponding to the first sensory stimulation signal. The instructions can further include directing an electrical signal to a neural population of the patient at a frequency in a frequency range of 1.5 kHz to 100 kHz, and directing a second sensory stimulation signal to the patient to elicit a second sensory response, while or after directing the electrical signal to the patient. The instructions can further include receiving an indication of a second sensory threshold of the patient corresponding to the second sensory stimulation signal and, if the second sensory threshold is less than the first, performing at least one of the following actions. A first action includes identifying a patient as a candidate for receiving an electrical therapy signal at a frequency in a frequency range of 1.5 kHz to 100 kHz, and a second action includes changing a signal delivery parameter in accordance with which the patient receives therapy via the electrical signal.

In further particular embodiments, the signal generator includes an implantable signal generator, and at least a portion of the computer readable medium is carried by the implantable signal generator. In other embodiments, at least a portion of the computer readable medium is external to the implantable signal generator. The first sensory stimulation signal can have a frequency of less than 1500 Hz, for example, 1 Hz.

From the foregoing, it will be appreciated that specific embodiments of the present technology have been described herein for purposes of illustration, but that various modifications may be made without deviating from the present technology. For example, embodiments of the simulations described above were performed in the context of simulating a demyelinated axon sheath. In other embodiments, neural degeneration can be simulated in other manners. Such manners can include other techniques for reducing the excitability of the neuron as a way of simulating a neuropathic condition. Particular embodiments were described above in the context of electrical signals applied to the patient's spinal cord neurons. In other embodiments, such signals (used for screening and/or therapy) can be applied to the patient's peripheral nerves. Certain aspects of the technology described in the context of particular embodiments may be combined or eliminated in other embodiments. For example, the process of screening a patient can be conducted separately from the process of treating the patient using a high frequency therapy signal. In other embodiments, the process of screening the patient may be conducted without applying a therapy to the patient, for example, if the patient fails the screening test. Further, while advantages associated with certain embodiments of the disclosed technology have been described in the context of those embodiments, other embodiments may also exhibit such advantages, and not all embodiments need necessarily exhibit such advantages to fall within the scope of the present technology. Accordingly, the disclosure and associated technology can encompass other embodiments not expressly shown or described herein.

To the extent any of the materials incorporated herein by reference conflict with the present disclosure, the present disclosure controls.

As used herein, the phrase "and/or" when used in the context of "a and/or b" means "a, or b, or both a and b."

I claim:

1. A method for identifying a patient as a candidate for pain treatment, comprising:
   identifying a first sensory threshold of the patient;
   directing an electrical signal to a neural population of the patient at a frequency in a frequency range of 1.5 kHz to 100 kHz;
   while and/or after directing the electrical signal to the patient, identifying a second sensory threshold of the patient; and
   if the second sensory threshold is less than the first sensory threshold, identifying the patient as a candidate for receiving an electrical therapy signal at a frequency in a frequency range of 1.5 kHz to 100 kHz.

2. The method of claim 1 wherein identifying the first sensory threshold includes applying a test signal via a signal delivery device implanted in the patient.

3. The method of claim 1 wherein identifying the first sensory threshold includes applying a test signal to the patient's skin.

4. The method of claim 1 wherein identifying the first sensory threshold includes applying a test signal to a peripheral nerve of the patient.

5. The method of example 1 wherein identifying the first sensory threshold includes applying a test signal to the patient's spinal cord.

6. The method of claim 1 wherein directing the electrical signal to the neural population of the patient includes delivering the electrical signal via a signal delivery device implanted in the patient.

7. The method of claim 1 wherein directing the electrical signal to the neural population of the patient includes delivering the electrical signal to the patient's spinal cord region.

8. The method of claim 1 wherein the electrical signal is subthreshold.

9. The method of claim 1, further comprising identifying suitable stimulation parameters for the patient, if the second sensory threshold is less than the first sensory threshold.

10. A method for treating a patient, comprising:
    directing a first electrical signal to a neural population of the patient in accordance with a first set of signal delivery parameters, including a frequency in a frequency range of 1.5 kHz to 100 kHz;
    identifying a first sensory threshold of the patient;
    directing a second electrical signal to the patient in accordance with a second set of signal therapy parameters different than the first;
    while and/or after delivering the second electrical signal to the patient, identifying a second sensory threshold of the patient; and
    if the second sensory threshold is less than the first sensory threshold, performing at least one of the following actions:
       identifying the patient as a candidate for receiving an electrical therapy signal in accordance with the second set of signal delivery parameters; or
       directing the electrical therapy signal to the patient in accordance with the second set of signal delivery parameters.

11. The method of claim 10 wherein identifying the first sensory threshold includes applying a test signal via a signal delivery device implanted in the patient.

12. The method of claim 10 wherein identifying the first sensory threshold includes applying a test signal to the patient's spinal cord.

13. The method of claim 10 wherein directing the first electrical signal to the neural population of the patient includes delivering the first electrical signal via a signal delivery device implanted in the patient.

14. The method of claim 10 wherein directing the first electrical signal to the neural population of the patient includes delivering the first electrical signal to the patient's spinal cord region.

15. The method of claim 10 wherein the first electrical signal is subthreshold.

16. The method of claim 10 wherein the first electrical signal produces a first therapeutic benefit to the patient, and the second electrical signal produces a second therapeutic benefit to the patient, the second therapeutic benefit being greater than the first.

17. A system for treating a patient, comprising:
    a signal generator that includes signal generation circuitry; and
    a computer-readable medium operatively coupled to the signal generation circuitry and programmed with instructions that, when executed:
       direct a first sensory stimulation signal to the patient to elicit a first sensory response;
       receive an indication of a first sensory threshold of the patient corresponding to the first sensory stimulation signal;
       direct an electrical signal to a neural population of the patient at a frequency in a frequency range of 1.5 kHz to 100 kHz;
       while and/or after directing the electrical signal to the patient, direct a second sensory stimulation signal to the patient to elicit a second sensory response;
       receive an indication of a second sensory threshold of the patient corresponding to the second sensory stimulation signal; and
       if the second sensory threshold is less than the first sensory threshold, perform at least one of the following actions:

identify the patient as a candidate for receiving an electrical therapy signal at a frequency in a frequency range of 1.5 kHz to 100 kHz; or change a signal delivery parameter in accordance with which the patient receives therapy via the electrical therapy signal.

18. The system of claim 17 wherein the signal generator includes an implantable signal generator.

19. The system of claim 18 wherein at least a portion of the computer-readable medium is carried by the implantable signal generator.

20. The system of claim 18 wherein at least a portion of the computer-readable medium is external to the implantable signal generator.

21. The system of claim 17 wherein the first sensory stimulation signal has a frequency less than 1,500 Hz.

22. The system of claim 21 wherein the first sensory stimulation signal has a frequency of 1 Hz.

23. The system of claim 17 wherein the first and second sensory stimulation signals have the same frequency and different amplitudes.

24. The system of claim 17, further comprising a signal delivery device coupleable to the signal generator.

25. The system of claim 24 wherein the signal delivery device is implantable.

26. The system of claim 24 wherein the signal delivery device includes an implantable percutaneous lead.

27. The system of claim 24 wherein the signal delivery device includes an implantable paddle.

28. The system of claim 24 wherein the signal delivery device includes a first signal delivery electrode and a second signal delivery electrode, and wherein the signal delivery device is coupleable to the signal generator to receive the first sensory stimulation signal at the first signal delivery electrode and the electrical signal at the second signal delivery electrode.

29. The method of claim 1, further comprising comparing the first sensory threshold to the second sensory threshold.

30. The method of claim 1 wherein identifying the first sensory threshold includes identifying the first sensory threshold using a sensitivity test, and wherein the identifying the second sensory threshold includes identifying the second sensory threshold using the sensitivity test.

* * * * *